US005790692A

United States Patent [19]
Price et al.

[11] Patent Number: 5,790,692
[45] Date of Patent: Aug. 4, 1998

[54] METHOD AND MEANS OF LEAST SQUARES DESIGNED FILTERS FOR IMAGE SEGMENTATION IN SCANNING CYTOMETRY

[75] Inventors: Jeffrey H. Price, 8568 Villa La Jolla Dr. #290, La Jolla, Calif. 92037-2334; David A. Gough, Cardiff, Calif.

[73] Assignee: Jeffrey H. Price, La Jolla, Calif.

[21] Appl. No.: 820,442

[22] Filed: Mar. 12, 1997

Related U.S. Application Data

[63] Continuation of Ser. No. 330,205, Oct. 26, 1994, abandoned, which is a continuation-in-part of Ser. No. 302,044, Sep. 7, 1994, Pat. No. 5,548,661.

[51] Int. Cl.[6] .................................................. G06K 9/00
[52] U.S. Cl. .......................... 382/133; 382/173; 382/205; 382/265
[58] Field of Search ................................ 382/133, 173, 382/205, 219, 220, 261, 265, 274, 279

[56] References Cited

U.S. PATENT DOCUMENTS

| | | | |
|---|---|---|---|
| 4,330,833 | 5/1982 | Pratt et al. | 382/318 |
| 4,342,905 | 8/1982 | Fujii et al. | 250/201 |
| 4,829,374 | 5/1989 | Miyamoto et al. | 358/93 |
| 5,027,420 | 6/1991 | Takebayashi et al. | 382/274 |
| 5,107,422 | 4/1992 | Kamatsky et al. | 382/274 |
| 5,121,444 | 6/1992 | Takizawa et al. | 382/219 |
| 5,239,170 | 8/1993 | Hughlett | 250/201.3 |

FOREIGN PATENT DOCUMENTS

| | | | |
|---|---|---|---|
| 0 163 394 | 9/1985 | European Pat. Off. | G02B 21/24 |

OTHER PUBLICATIONS

N.R. Pal et al., "A Review On Image Segmentation Techniques", *Pattern Recognition*, vol. 26, Nos. 9, pp 1277–1294, 1993.

P. Nickolls, et al. "Pre-Processing Of Images In An Automated Chromosome Analysis System", *Pattern Recognition*, vol. 14, Nos. 1–6, pp. 219–229, 1981.

W.A. Carrington, et al. "Three–Dimensional Imaging On Confocal And Wide–Field Microscopes", *Confocal Microscopy Handbook*, Chapter 14, pp. 151–161.

D.A. Agard, et al. "Fluorescence Microscopy In Three Dimensions", *Methods in Cell Biology*, vol. 30, pp. 353–377.

S. Hamada, et al. "DAPI Staining Improved For Quantitive Cytofluorometry", *Histochemistry*, 1983, pp. 219–226.

A.K. Jain, "Digital Image Processing", *Proceedings of the IEEE*, vol. 69 No. 5, pp. 502–581, 1981.

Introduction, "Digital Image Processing", *Proceedings of the IEEE*, vol. 69 No. 5, pp. 1–7, 1981.

B.H. Mayall, "Current Capabilities And Clinical Applications Of Image Cytometry", *Cytometry Supplement*, vol. 3 pp. 78–84, 1988.

(List continued on next page.)

*Primary Examiner*—Joseph Mancuso
*Assistant Examiner*—Timothy M. Johnson
*Attorney, Agent, or Firm*—Gray Cary Ware Freidenrich, LLP

[57] ABSTRACT

In an image segmentation system that processes image objects by digital filtration, a digital filter is defined. The digital filter includes a neighborhood operator for processing intensity values of neighborhoods of pixels in a pixel array. A first pixel array is received defining a pixelated image including one or more objects and a background and a second pixel array is received that defines a reference image. The reference image includes at least one object included in the pixelated image in a background. In the reference image, pixels included in the at least one object are distinguished from pixels included in the background by a predetermined amount of contrast. Pixels of the first and second images are compared to determine a merit value; the merit value is used to compute neighborhood operator values; and, the neighborhood operator is applied to images in order to create or enhance contrast between objects and background in the images.

23 Claims, 16 Drawing Sheets

OTHER PUBLICATIONS

C.J. Herman, et al, Recent Progress In Clinical Quantitative Cytology, *Arch Pathol Lab Med*, vol. 111, pp. 505–512, Jun., 1987.

J.P.A. Baak, "Quantitative Pathology Today —A Technical View", *Path. Res. Pract.*, vol. 182, pp. 396–400.

J. Price, et al, "Nuclear Recognition In Images Of Fluorescent Stained Cell Monolayers", *SPIE*, Col 1349, pp. 294–300.

S.J. Lockett, et al, "Automated Fluorescence Image Cytometry As Applied To The Diagnosis And Understanding Of Cervical Cancer", *Optical Microscopy*, pp. 403–431.

J. Price, "Scanning Cytometry For Cell Monolayers", *A Dissertation in Bioengineering*, UCSD, 1990.

K.S. Fu, et al, "A Survey On Image Segmentation", *Pattern Recognition*, vol. 13, pp. 3–16, 1981.

S.E. Reichenbach, et al, "Optimal, Small Kernels For Edge Detection", *IEEE Proc. 10th Int. Conf. Pattern Recognition*, 57–63, 1990.

R.O. Duda, et al, *Pattern Classification and Scene Analysis*, "Linear Discriminant Functions" Chapter 5, pp. 130–188.

S. Haykin, *Adaptive Filter Theory*, Second Edition, pp. 766–769.

J.C. Russ, *The Image Processing Handbook*, Segmentation and Thresholding, pp. 238–243.

P.O. Amblard et al, "Frequency Domain Volterra Filters In Terms Of Distributions", *IEEE Signal Processing Letters*, vol. 1, No. 11, Nov., 1994.

W.E. Blanz, et al, "Control–Free Low–Level Image Segmentation: Theory, Architecture, And Experimentation", *Advances in Machine Vision*, pp. 255–282.

Gonzalez et al., Digital Image Processing, 1992, pp. 452–455, Textbook.

S. Haykin, Adaptive Filter Theory, 1991, pp. 766–767.

"A Survey On Image Segmentation" by K.S. Fu & J.K. Mui, *Pattern Recognition*, vol. 13, Pergamon Press Ltd., 1981, pp. 3–16.

"A Review On Image Segmentation Techinques", by Nikhil R. Pal & Sankar K. Pal, *Pattern Recognition*, vol. 26, No. 9, Pergamon Press Ltd., 1993, pp. 1277–1294.

"The Image Processing Handbook", by John C. Russ, Second Edition, CRC Press 1995, pp. 347–405.

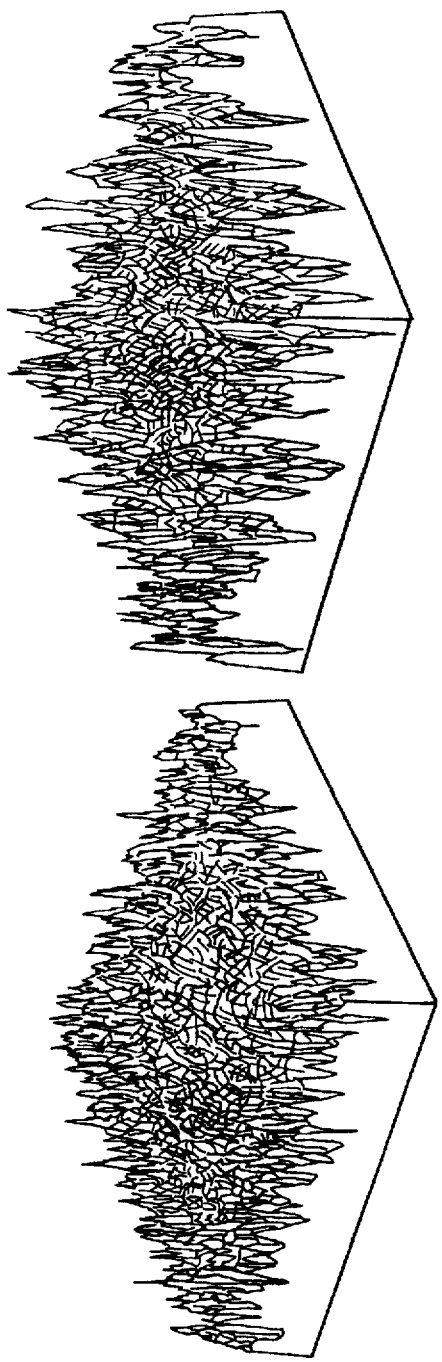
FIGURE 17b
FIGURE 17a
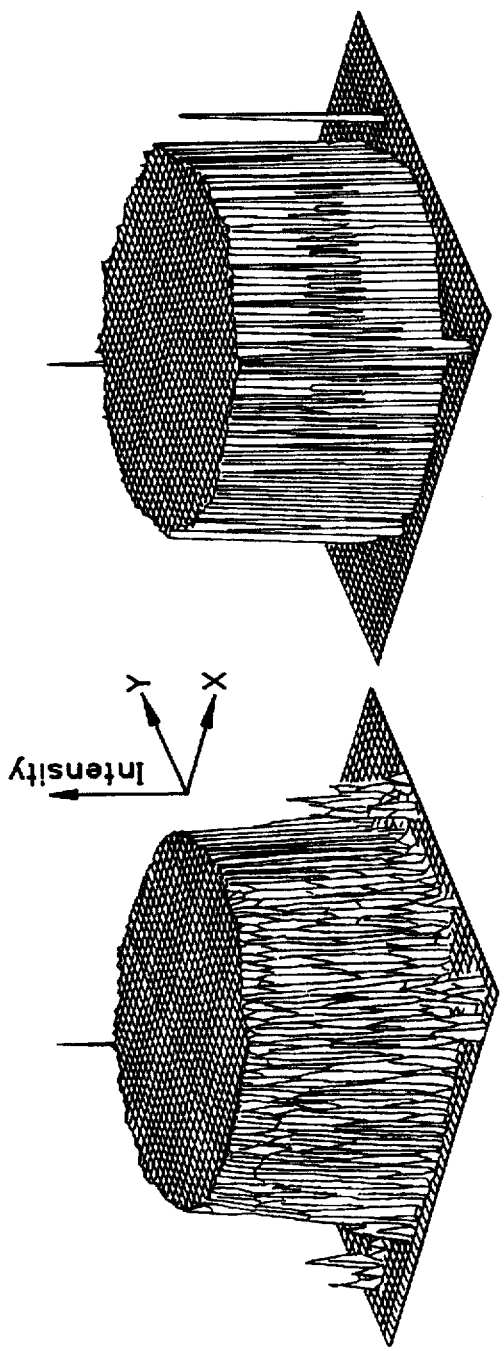
FIGURE 17d
FIGURE 17c

METHOD AND MEANS OF LEAST SQUARES DESIGNED FILTERS FOR IMAGE SEGMENTATION IN SCANNING CYTOMETRY

CROSS REFERENCE TO RELATED APPLICATIONS

This application is a continuation of application Ser. No. 08/330,205, filed Oct. 26, 1994, now abandoned, which is a continuation-in-part of U.S. patent application Ser. No. 08/302,044, U.S. Pat. No. 5,548,661, for "OPERATOR INDEPENDENT IMAGE CYTOMETER" filed Sep. 7, 1994.

BACKGROUND OF THE INVENTION

1. Field of the Invention

The present invention relates to image segmentation and, more particularly, to a system for segmentation of images obtained through a microscope.

2. Description of the Related Technology

Fully automated scanning of large numbers of cells under the light microscope could yield important diagnostic and research information for many biomedical applications. Analysis of images of cell nuclei stained with a fluorescent dye, for example, could yield the quantities of DNA, as well as nuclear sizes, shapes and positions. Accurate measurements of these cellular parameters would have application to PAP smear screening and other clinical diagnostic instruments, as well as many basic science and pharmacological research applications. A critical capability of such a system is segmentation of the objects of interest from background and image artifacts. In this regard, "segmentation" refers to partitioning an image into parts ("segments") that may be individually processed. Preferably, the segments of interest, which may also be referred to as "objects", are individual cells.

Once segmented, the binary image would be analyzed for size and shape information and overlaid on the original image to produce integrated intensity and pattern information. Because of the inherent biologic variability it would be advantageous to process large numbers of cells ($10^4$–$10^6$), in many applications. Accurate analysis of large numbers of cells is particularly important in PAP smear screening, where measurement of all of the cells on the slide is required to avoid false negative diagnoses. At this scale, the intervention of a human operator is impractical and expensive. A system capable of these tasks therefore requires accurate, real time segmentation in order to achieve the level of operator independent automation required for practical analysis of the thousands of images on each slide.

The following references address various aspects of automated cell scanning:

J. P. A. Baak, "Quantitative pathology today—a technical view," *Path. Res. Pract.*, 182, 396–400 (1987).

C. J. Herman, T. P. McGraw, R. H. Marder and K. D. Bauer, "Recent progress in clinical quantitative cytology," *Arch. Pathol. Lab. Med.*, 111, 505–512 (1987).

S. J. Lockett, M. Siadat-Pajouh, K. Jacobson and B. Herman, "Automated fluorescence image cytometry of cervical cancer," in *Optical Microscopy, Emerging Methods and Applications*, B. Herman and J. J. Lemasters, eds., San Diego: Academic, 403–431 (1993).

B. H. Mayall, "Current capabilities and clinical applications of image cytometry," *Cytometry Supplement*, 3, 78–84, (1988).

J. H. Price and D. A. Gough, "Nuclear Recognition in Images of Fluorescent Stained Cell Monolayers," *Proceedings of the International Society for Optical Engineering (SPIE), Applications of Digital Image Processing XI*, pp. 294–300, Jul. 12, 1990.

J. H. Price, *Scanning Cytometry for Cell Monolayers*, Ph. D. Dissertation, University of California, San Diego (1990).

A number of previous image segmentation methods evaluated for possible application to automated image cytometry. In a review of segmentation for cell images, the methods were categorized as thresholding or clustering, edge detection and region extraction. See K. S. Fu and J. K. Mui, "A survey on image segmentation," *Pattern Recognition*, 13, 3–16 (1981). Global thresholding is simple and can be implemented in real time, but choosing the best threshold can be difficult and different objects may require different thresholds. The iterative and heuristic nature of clustering makes it difficult to implement in real time. Edge detection is usually a two step process with, for example, a gradient filter in the first step followed by edge connection in the second step. The filter can be applied in real time, but reconstructing broken edges and eliminating false ones can be computationally intensive. In another review covering a broader set of applications, the following classes of image segmentation techniques were added: relaxation, Markov Random Field based approaches, neural network based approaches, surface based segmentation, and methods based on fuzzy set theory. See N. R. Pal and S. K. Pal, "A review on image segmentation techniques," *Pattern Recognition*, 26, 1277–1293 (1993). These additional classes are all computationally intensive, with neural network based approaches the only class previously implemented in real time. Real time neural network implementations, however, require additional hardware beyond the more conventional image processing hardware considered here.

The error criteria for evaluating image segmentation are sometimes based on the success of object classification. For fluorescent stained cells, however, dye specificity can be thought of as having performed initial object classification. When a preparation is stained with a DNA-specific fluorescent dye and rendered into a pixelated image, for example, the assumption can be made that a group of pixels in the image is an object of interest if it is bright. Such fluorescent stained cell nuclei typically exhibit nonuniform intensity, size, shape and internal structure. Correct measurement of these characteristics depends on accurate segmentation of the pixelated image. One measurement, the DNA content of a cell nucleus, is made by integrating object intensity, which depends on the segmented group of pixels. The cell count, on the other hand, would have very little dependence on segmentation. Rather than simple counting, the goal for an automated system is segmentation that will lead to accurate integrated intensity, morphology and pattern measurements. Further classifications could then be based on this quantitative data. These classifications would be advantageous for studies in cell physiology and cytopathology because they would be based on characteristics that relate directly to the biological state of the cells (e.g., DNA content as a measure of position in the cell division cycle), rather than simply subjective appearance. Since the error of these measurements decreases with image segmentation accuracy, evaluation may be based on pixel classification into object and background. Similar explicit error criteria for image segmentation have been previously discussed. (N. R. Pal et al., op.cit.)

With this background and goal in mind, the inventors have evaluated simple intensity thresholding of images of fluorescent stained nuclei. Problems with thresholding arise, however, because in images of fluorescent stained cells the nuclei vary markedly in intensity, with the biggest differences, for example, between the large, dim resting nuclei and the condensed, bright dividing nuclei. Selection of a single low threshold for segmentation can cause incorrect inclusion of a portion of the nearby background in bright objects, whereas the single high threshold required to correctly segment bright nuclei can cause portions of the dim nuclei to be deleted. Filtering the images with generic edge, sharpen or bandpass filters as taught by P. Nickolls, J. Piper, D. Rutovitz, A. Chisholm, I. Johnstone and M. Robertson in "Pre-processing of Images in an Automated Chromosome Analysis System," (*Pattern Recognition*, vol. 14, pp. 219–229, 1981) does not help significantly because of the difficulty in separating edge frequencies from those of the internal features of the nuclei. Due to the structure in the nuclei, bandpass filters tend to break the objects into pieces or cause indentations at the edge. For example, consider the sample image with a pair of fluorescent stained nuclei that is shown in FIG. 1. In this image there is a substantial difference in brightness between the (bright) smaller mitotic nucleus 12, entering cell division, and the (dim) larger resting nucleus 14. The objects 12, 14 in FIG. 1 have respective object borders at different intensities and could not be correctly segmented by one global threshold. There is also obvious structure in the dim nucleus 14, with internal edges that create problems for conventional sharpening filters.

SUMMARY OF THE INVENTION

To address these problems, the inventors provide a model consisting of a convolution filter followed by thresholding, with the best filter being obtained by least squares minimization. Since commercially available hardware contains real time convolution in pipeline with thresholding, this model satisfies the speed requirement. Least squares filter design theory classically requires specific knowledge of the desired transfer function or impulse response (A. V. Oppenheim and R. W. Schafer, *Discrete-Time Signal Processing*, New Jersey: Prentice Hall, 1989; R. A. Roberts and Clifford T. Mullis, *Digital Signal Processing*, Menlo Park: Addison-Wesley, 1987). For example, in classical communications processing, deconvolution of serial data passed through a corrupting channel is accomplished by proposing the form of the corrupting function, and then approximating a stable inverse. (R. A. Roberts and Clifford T. Mullis, *Digital Signal Processing*, Menlo Park: Addison-Wesley, 1987). The transfer function has also been included with noise and sampling in a linear model for finding optimal (minimum mean square error), small kernel convolutions for edge detection. (S. E. Reichenbach, S. K. Park and R. A. Gartenberg, "Optimal, Small Kernels for Edge Detection," *IEEE Proc. 10th Int. Conf. Pattern Recognition*, 57–63, 1990). However, the method of the invention is unique in that the design specifications do not include a specific response function, but only knowledge of the input and output, with a user-defined ideal as the output image. The transfer function that leads to the best image segmentation is found directly. The critical insight made in this invention was to think of the transfer function as incorporating the necessary components of the inverse of the transfer function of the system that blurred, sampled and added noise to the image with the segmentation constraints imposed by thresholding.

This approach differs from prior art image modeling by its incorporation of a classification step. Relatedly an "image model" can be thought of as " . . . any analytical expression that explains the nature and extent of dependency of a pixel intensity on intensities of its neighbors". (R. Chellappa, Introduction to "Chapter 1: Image Models," in *Digital Image Processing*. Los Alamitos: IEEE Computer Society Press, 1–8 (1992)). Image models have been adapted for image segmentation, and linear filters have been considered as image models. (A. K. Jain, "Advances in Mathematical Models for Image Processing," *Proceedings of the IEEE*, 69:2, 502–528 (1981)). The inventors have realized that it also is useful, however, to take advantage of the fact that what is being modeled is the transformation of each pixel into a segmented value corresponding to the class of object to which it belongs. The resulting "image segmentation model" can be defined as any analytical expression that explains the nature and dependency of a segmentation identity of a pixel on its intensity and the intensities of its neighbors.

A critical insight which the inventors had in making the invention was that digital filtration, when applied to image segmentation, became a classification step. This realization meant that the design of filters according to the invention could take advantage of classification tools in technical areas that are not related to cytometry. One such classification tool is the perceptron criterion used in neural networks that classify patterns. (Richard O. Duda and Peter E. Hart, *Pattern Classification and Scene Analysis*, John Wiley & Sons: New York, pp. 130–186, 1973). In this regard, the perception criterion incorporates minimum object-background contrast into an error function that is used to classify scene features. Use of the perceptron criterion in the invention requires iterative, non-linear solution of the filter parameters. The requirement of the method of the invention that the resulting filtered image consist, for example, of object pixels of intensity $\geq 255$ and background pixels $\leq 0$ with a minimum of error, corresponds to a perceptron criterion of 128 with a "margin" of $-128$, $+127$. The Duda and Hart reference also covers the Perceptron Convergence Theorem, in which convergence of the minimization search is proven for linear classifiers. Convolution and Fourier filters are linear functions, so the convergence theorem applies.

This specific image segmentation model was chosen by the inventors to determine if incorporation of the classification step can result in accurate segmentation for a filter that can be implemented in real time. The specific hypothesis tested was that optimally designed convolution is adequate for segmentation of fluorescent nuclear images exhibiting high object-to-object contrast and internal structure. This hypothesis led to a novel method for generating an optimal segmentation filter for the hardware available and under whatever other conditions may be imposed. Linear least squares for an exact input-output fit, nonlinear least squares for minimizing the error from minimum object-background contrast, and weighted error for enhancing edge contribution, were successively incorporated to derive as much benefit as possible from small kernel convolution filtering. The image segmentation errors for each of these methods are presented and compared.

During experiments with linear filters by the inventors, it was noted that while linear filters would be capable of solving many of the image segmentation problems associated with fluorescence microscopy images, they are likely to fail for segmentation of images collected with the many transmitted light microscopy techniques. These include brightfield, phase contrast, differential interference contrast (DIC, or Nomarski), and darkfield. Even more complicated image segmentation challenges arise in electron microscope images. The limitations of linear filters in these applications arise from the fact that differences between object and background, or between different objects, are due to higher order image characteristics such as contrast (measured by intensity standard deviation or variance), or even higher order statistics. The inventors then concluded that just as the convolution neighborhood operators are capable of raising the contrast between a bright object and its dark background, the analogous second order neighborhood operator should be capable of transforming objects differing only in contrast (with no first order statistical differences) into objects segmentable by intensity thresholding. This hypothesis was explored by extension of the perceptron criterion to design of second order filters for segmentation of images consisting of areas of Gaussian random noise differing only in the standard deviation of the noise. This second order neighborhood operator is known as a second order Volterra series. Vito Volterra first studied this series around 1880 as a generalization of the Taylor series (Simon Haykin, *Adaptive Filter Theory*, Prentice Hall: Englewood Cliffs. pp. 766–769, 1991). Like the Taylor series, the Volterra series continues to higher order terms. Just as image objects differing in contrast were segmented with much higher pixel classification accuracy by perceptron criterion design of a second order Volterra filter than previous methods, objects characterized by higher order statistics will be accurately segmented with the corresponding higher order Volterra series. Thus the methods invented here will be generally applicable to a wide range of transmitted light and electron microscopy images. Where similar problems arise in segmenting patterns collected from other instruments, such as in satellite imagery, robotics and machine vision, these techniques will also apply.

In summary then, the present solution to the problem of fast and accurate image segmentation of fluorescent stained cellular components in a system capable of scanning multiple microscope fields, and accurate segmentation of transmitted light microscopy and electron microscopy images, is the image segmentation system of the invention, which is designed to automate, simplify, accelerate, and improve the quality of the process. The principal objective of the image segmentation system is to accurately and automatically separate the areas of an image from the microscope into the objects of interest and background so as to gather information and present it for further processing.

BRIEF DESCRIPTION OF THE DRAWINGS

FIG. 17 illustrates segmentation results achieved with a second order Volterra filter.

DETAILED DESCRIPTION OF THE PREFERRED EMBODIMENTS

The following detailed description of the preferred embodiments presents a description of certain specific embodiments to assist in understanding the claims. However, the present invention can be embodied in a multitude of different ways as defined and covered by the claims.

MATERIALS AND METHODS

A. Cells and Specimen Preparation

NIH 3T3 cells were plated on washed, autoclaved #1.5 coverslips. The cells were maintained in Eagle's minimal essential medium with Earle's salts, supplemented with 10% fetal bovine serum, 100 μg/ml gentamicin, and 0.26 mg/ml L-glutamine (final concentrations), in a humidified 5% $CO_2$ incubator at 37° C. After 1 day of growth, the coverslips were washed in phosphate buffered saline (PBS), fixed for 30 minutes in 4% paraformaldehyde in 60% PBS, and stained for one hour. The stain solution consisted of 50 ng/ml 4',6-diamidino-2-phenylindole dihydrochloride (DAPI, Molecular Probes, Eugene, Oreg.), 10 mM TRIS, 10 mM EDTA, 100 mM NaCl, and 1% 2-mercaptoethanol [S. Hamada and S. Fujita, "DAPI staining improved for quantitive cytofluorometry," *Histochem.*, 79, 219–226 (1983)]. This preparation was found to have excellent antiphotobleaching properties. After staining, a few drops of DAPI solution were placed on a glass slide, the coverslips were laid over the solution, the excess solution was wicked away with tissue, and the coverslip sealed to the slide with nail polish.

B. Computer System and Software

Figure 2:
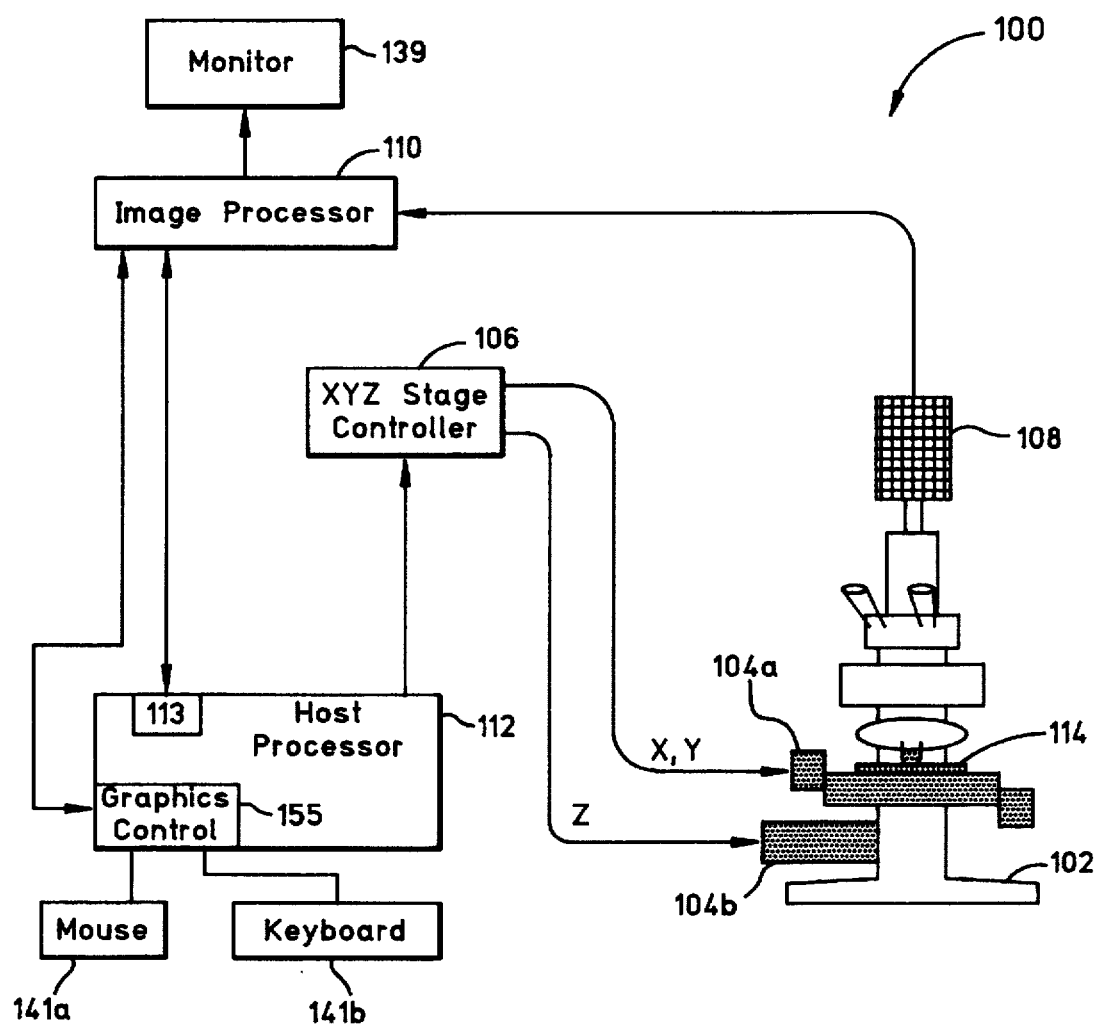
FIG. 2 is a block diagram of a presently preferred embodiment of an automated image cytometer in which the present invention is embodied.

FIG. 2 illustrates an operator-independent image cytometer 100 in which the present invention operates to image cells prepared as described above. The hardware components of the cytometer 100 include an epifluorescent microscope 102, a motorized stage 103 controlled by a pair of XY motors 104a and a Z motor 104b, XYZ stage controller 106, a video camera 108, an image processor 100, and a host computer 112.

The microscope 102 is preferably a Nikon Optiphot microscope including a CF Fluor DL 20× C, 0.75 NA objective with Ph3 phase contrast. This fluorite objective provides high UV transmission. The epifluorescence system utilized an Osram 100w HBO W/2 mercury vapor arc lamp and a filter cube with a 365 nm±10 nm (50% of peak) bandpass excitation filter, a 400 nm dichroic mirror and no barrier filter. The video camera 108 that collected the images was a Dage VE1000 RS-170 CCD camera.

The host computer 112 is preferably a microcomputer such as an AT compatible i486 machine with RAM memory and a hard drive (not shown) available as a unit from Datel (San Diego, Calif.). The host computer 112 controls the image processor 110 and the motorized stage 103 (which may comprise a motorized stage available from New England Affiliated Technologies of Lawrence, Mass.). The host computer 112 communicates with the image processor 110 by way of an interface board (supplied with the image processor 110 and plugged into an expansion slot in the host computer 112). The host computer 112 communicates with stage controller 106 by way of a controller board to move the stage 103 and the X, Y directions for lateral positioning and in the Z direction for autofocus. The stage 103 is moved under the control of the host computer 112 so that portions or fields of a specimen 114 can be examined.

Figure 3:
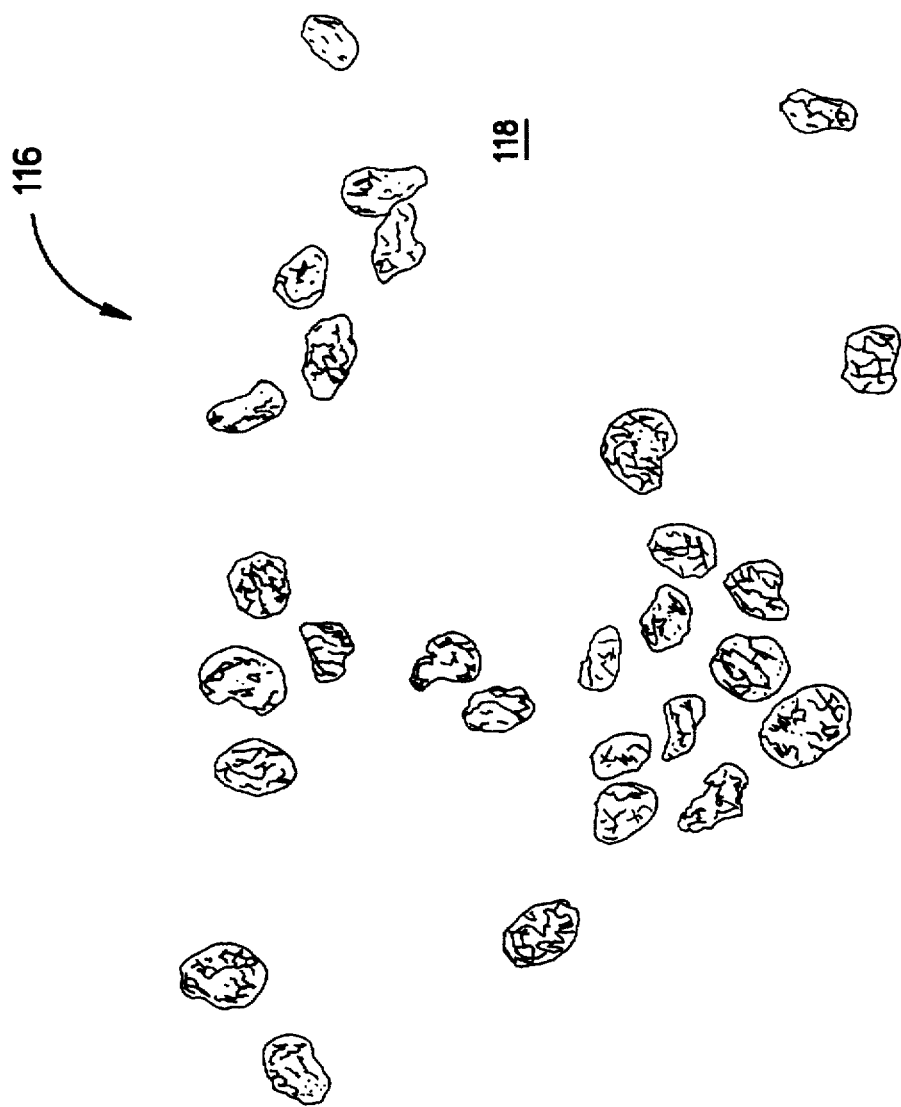
FIG. 3 is a representation of the magnified image of cells as seen through the microscope of the cytometer shown in FIG. 2.

A portion of an example specimen, such as the specimen 114 of FIG. 2, is shown in FIG. 3. FIG. 3 represents a magnified image of a specimen comprising a set of cells, particularly cell nuclei, generally indicated at 116. Preferably, the cells are prepared as described above.

The fluorescent staining of the cells produces increased light intensity in the cell nuclei. The representation of FIG. 3 shows the cells, or cell nuclei 116, in a reverse or negative image as darker regions against a light background 118. However, it should be understood that the positive, or "normal" image will have the cells 116 appear as light regions against a dark background. Henceforth, a reference to an image will refer to such a normal image.

It should be noted that the cells 116 do not share the same intensity from one cell to another, or even from one point within a single cell to another. Hence, segmenting the cells 116 from the background 118 for further processing by a computer cannot be performed by using only an intensity thresholding technique.

Figure 4:
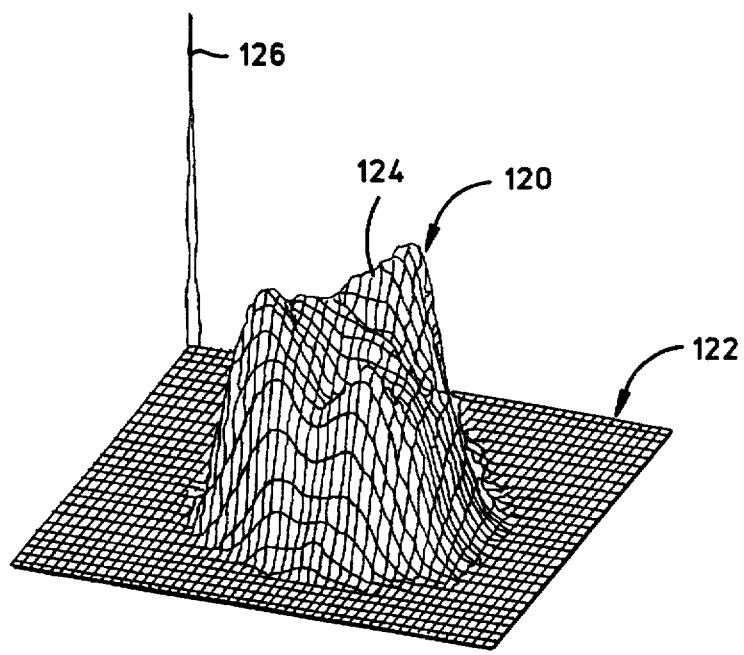
FIG. 4 is a 3-dimensional plot of the gray-scale object that is representative of a cell.

FIG. 4 shows a 3-dimensional plot of gray-scale digital image of a cell (such as one of the cells 116 shown in FIG. 3), but here the cell is shown in its normal image form of higher white intensity on a lower intensity background. Note that after the image of one or more cells is received by the video camera 108 and digitized by the image processor 110, each digitized cell is then referred to as an object 120. The area surrounding the object 120 is termed a background 122. The X, Y plane of the plot corresponds to the X, Y plane of the stage 103 (FIG. 2). The Z, or vertical, axis represents light intensity. The plot is divided into small units commonly referred to as pixels as is indicated in FIG. 4, for example, by a pixel 124. A scaling spike 126, representing the maximum intensity, is located at one corner of the plot. The plot clearly shows the variation of the intensity commonly found within a single cell.

A fundamental problem that is addressed by the present invention is image separation, that is, separating many objects, such as 120, from the image background 122 so that the cells 116 (FIG. 3) can thereafter be analyzed by a computer. The process of image segmentation begins when an array of pixels representing the magnified image is fed from the CCD camera 108 (FIG. 2) to the image processor 110. Herein, an array of pixels (digital or analog) that represents an image may also be referred to as a "pixelated image".

Figure 5:
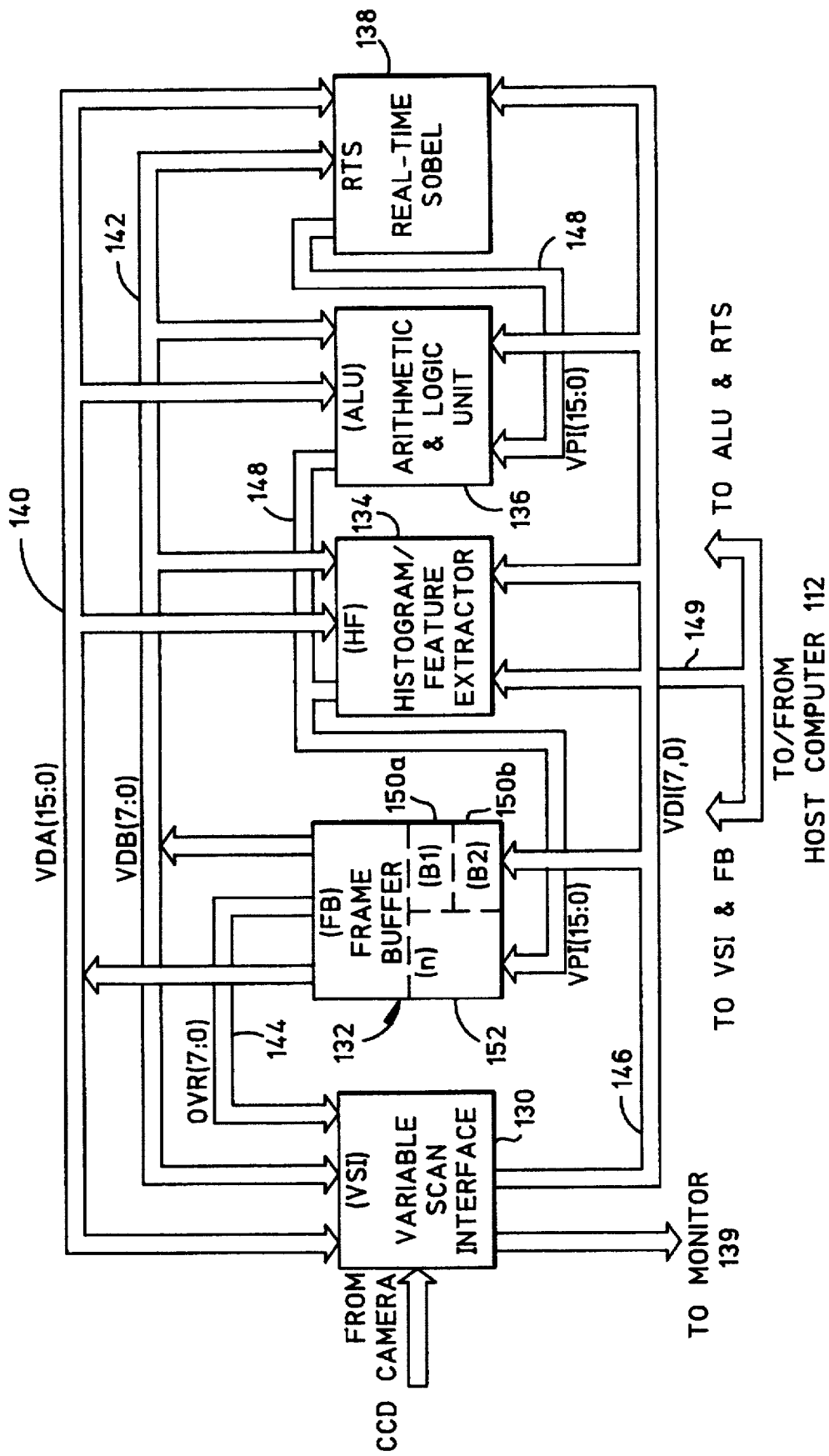
FIG. 5 is a block diagram of the presently preferred image processor of FIG. 2.

A block diagram of the preferred image processor 110 is illustrated in FIG. 5. It should be observed that while an image processor will generally speed up the image segmentation of the present invention, there is no reason why the calculations performed therein could not take place in the host computer 112 (FIG. 2) or any other computer.

The image processor 110 is preferably an Imaging Technology, Inc. Series 151 image processor, and is preferably configured with five functional units, or boards, as follows: (1) a variable scan interface (VSI) 130, for analog-to-digital (A/D) conversion of RS-170 video signals generated by the camera 108 (FIG. 2) and digital-to-analog (D/A) conversion of the stored imaes to display on the monitor 139; (2) a frame buffer (FB) 132, for storage of one 16-bit and two 8-bit digital images, each in the form of a respective 512×512 array of pixels; (3) a histogram/feature extractor (HF) 134, for creating histogram and feature arrays; (4) an arithmetic & logic unit (ALU) 136, for multiplication, addition, subtraction, logical operations, and bit shifts; (5) a real time sobel (RTS) 138, with a convolver for 8×8 or smaller convolutions.

The preferred image processor 110 performs all operations in real time (1/30th second), or faster in area-of-interest (AOI) mode. The AOI mode allows select processing of only a portion of the digital image. The time required for AOI mode operations is proportional to the number of pixels, or picture elements, in the selected region.

Understanding the basic mechanisms by which the five image processor boards 130, 132, 134, 136, 138 communicate and function is important for understanding the present invention. Image operations, such as subtraction, multiplication, and convolution are carried out by the ALU 136 and RTS 138. The ALU 136 and RTS 138 are pipeline processors. This means that image information flows into these boards 136, 138, is operated on, and flows out. The image information is always flowing. If the ALU 136 is set up for multiplication of two images stored in the FB 132, then one multiplication is occurring every 33 milliseconds as long as the set-up remains and the image processor 110 is powered on. Control is maintained by having the host processor 112 instruct the FB 132 to acquire the information coming from the processors 130, 136, 138. From the point of view of the FB 132, information flows out over three buses, video data A (VDA) 140, video data B (VDB) 142, and overlay (OVR) 144, and in over two buses, video data in (VDI) 146 and video pipeline in (VPI) 148. The FB 132 is always broadcasting information over its output buses and information is always available to it over its input buses. If the instruction to acquire is not sent to the FB 132, the results of the operations are not stored. Programming the operations of the boards in the Series 151, therefore, is a matter of controlling the flow of image information as well as setting specific operations on or off.

The frame buffer 132 contains 1 Megabyte of random access memory organized as two 8-bit×512×512 image stores called, respectively, B1 150a and B2 150b, and one 16-bit×512×512 image stored called A, or FRAMEA, 152. FRAMEA 152 can also be treated as two 8-bit images. The VDA 140 continuously carries the 16-bit information stored in FRAMEA 152 and the VDG 142 continuously carries 8-bit information stored in either B1 150a or B2 150b. A multiplexer (not shown) controls which image is carried by the VDB 142, i.e., the image stored in B1 150a or B2 150b. Control over which image is operated on is maintained at the input to the pipeline processors 136, 138. The image output from the pipeline processors 136, 138 is available only on the 16-bit VPI 148. This processed VPI image information can be acquired directly only by FRAMEA 152. The 8-bit overlay bus (OVR) 144 is used to create an overlay for display of nuclei edges on the monitor 139 on the images stored in FRAMEA 152 and B1 150a using information stored in B2 150b.

The VSI 130 which converts video signal formats between analog and digital also acts as a simple pipeline processor. It has access to the VDA and VDB buses 140, 142 and can perform look-up table transformations on information from these buses and broadcast the transformed images over the VDI 146. The 8-bit VDI image information can be acquired directly by B1 150a or B2 150b, and indirectly by FRAMEA 152 through the pipeline processors 136, 138. The VDI 146 also carries the images acquired from the camera inputs, one of which is used for the CCD camera 108. Image transfer from B1 or B2 150 to FRAMEA 152 must be performed through the ALU 136 (with or without processing) and information from FRAMEA 152 can be transferred to B1 or B2 150 through the ADI 130.

Information can also be transferred between the image processor 110 and the host computer 112 on bus 149. In addition to reading image information in the form of pixel intensities, most of the registers (not shown) of the image processor 110 can be read to determine the operations currently set. Processed image information is available from only two sources: the ALU min/max registers and the HF 134. The ALU 136 can determine the minimum and maximum intensities in an image and the HF 134 provides more complicated processing, histogram compilation and feature extraction. The HF 134 provides no pipeline processing. Images read by the HF 134 are converted into information read only by the host processor 112. There are no image output buses carrying images altered by the HF 134.

Real-time histogram and feature extraction capabilities of the image processor 110 (FIG. 1) are important for timely operation of the cytometer 100. The histogram array (not shown), generated by the HF 134 in histogram mode, is an array containing the number of pixels in the image at each intensity (e.g., for an 8-bit pixel, gray-scale image, the intensity range if 0, representing minimum intensity, to 255, representing maximum intensity). The histogram can be used for intensity statistics. For example, obtaining the average and standard deviation in the image for the purpose of autofocus. In feature extraction mode, the HF 134 provides an organized array of all pixels at defined sets of intensities. As will be further discussed below, the groups of pixels or "streaks" are compressed by the HF 134 using the well-known method of run-length encoding (RLE). The Series 151 is programmed by writing to registers on the processing boards. A set of higher level routines is provided by the Series 151 Library.

The VSI 137 operates conventionally to convert pixelated images in the frame buffer 132 into RS-170 digital signals. Standard control means (not shown) are provided to select the 8-bit VDI image information from B1 150a or B2 150b for provision to the VSI 130.

The graphics unit 155 operates conventionally on pixelated images stored in B1 150a or B2 150b when they are displayed on the monitor 139. Preferably, the graphics unit 155 provides the functionality necessary to draw closed boundaries on image objects displayed on the monitor 139, to add a boundary to the array of pixels that correspond to the displayed image in either B1 150a or B2 150b, and to initiate arithmetic operations on pixel arrays in B1 150a and B2 150b in response to depression of function keys (not shown) on user interface devices such as a mouse 139a or a keyboard 139b. In this regard, the graphics unit operates on a four-bit overlay plane provided, for example, with B2 150b for storage of graphics information to be displayed on an image or image portion in B2 150b.

Programs implementing the invention were written in C, compiled with Metaware High C (Santa Cruz, Calif.) and linked by the Phar Lap (Cambridge, Mass.) 386 DOS Extender. Numerical Recipes in C subroutines were also made into a library with this compiler. The Imaging Technology Series 151 C Library source code was ported to ANSI C and recompiled with Metaware High C. This combination allowed use of the full 32-bit capability of the i486 CPU by programs running under 16-bit DOS. The software product embodying means executable by the host computer 112 are shown residing on a storage device 113 accessible to the host computer 112.

The method of the invention provides for definition of a type of digital filter implemented in the image processor 110. Preferably, the digital filter is a type that includes a neighborhood operator. In the preferred embodiment, the digital filter is a convolution filter whose neighborhood operator is a kernel. According to the method of the invention, a type of digital filter is first defined in terms of its neighborhood operator, with the definition including specification of the shape and size of the neighborhood operator. Next, a first array of pixels defining a pixelated image including one or more objects and a background is received. Then a second array of pixels defining a reference image is received, the reference image including at least one object included in the pixelated image defined by the first array and a background, in which pixels included in the object are distinguished from pixels included in the background by a predetermined amount of contrast. Next, pixels of the first pixel array are compared with pixels of the second pixel array to determine a merit value, with the merit value then being used to compute elements of the neighborhood operator. Last, the neighborhood operator is applied to image objects to create or enhance contrast between the objects and background.

In the preferred embodiment, the digital filter is a convolution filter with an 8×8 kernel whose elements are calculated in the host computer 112 and entered into the RTS 138. An image containing one or more objects (cells) is obtained by the cytometer system 100 (FIG. 2) and stored in B1 150a. This is referred to as the "original image". Next, an image corresponding to the original image is acquired and stored in B2 150b where it is processed to provide a reference image, which is also termed an "ideal image". In the preferred embodiment, one or more objects in the reference image are preprocessed to provide a predetermined contrast between the magnitudes of background pixels and object pixels. For example, the reference image may include a cell that is in the original image around whose periphery a user has traced a boundary using the mouse 141a on a representation of the reference image on the monitor 139. Once the boundary has been drawn around the periphery of the cell, a stroke of the first mouse function key superimposes the boundary onto the pixel array representing the reference image in B2 150b. Then, the user strokes a second mouse function key for setting all object pixels within the drawn boundary of the pixel array in B2 150b to a predetermined grayscale value (C) for cell pixels and all background pixels outside of the boundary to a predetermined background pixel grayscale value (B). These functions are conventionally executed by the graphics unit 155 and AU 136 by operating on the magnitude values of the pixels in the pixel array stored in B2 150b.

The inventors do contemplate other means for producing reference images, including, but not limited to images that have been processed using filters of preset values.

Next, values for the neighborhood operator of the defined digital filter are obtained by processing the original and reference images as discussed below. This processing is done in the host computer 112, which acquires the original and reference images from the frame buffer 132. In the preferred embodiment, an 8×8 kernel for a convolution filter is calculated by the host computer 112 and entered into the RTS 138. Once the digital filter in the image processor is configured with neighborhood operator values, image segmentation proceeds.

C. Construction of Ideal Images

For the images of fluorescent stained cell nuclei, the success of the image segmentation methods was evaluated by comparison with a user-defined ideal image. The subjective nature of definition by a human is a concern and it is desirable to obtain an independent objective standard. However, the ultimate standard is defined by human judgment because no better independent standard has been identified. (N. R. Pal et al., op cit.). A rough segmentation ideal was created by sharpening and thresholding and the mistakes edited pixel by pixel with a cursor overlaid on the monitor 139. The labor intensive nature of this approach could be reduced by using one of the more computationally intensive image segmentation methods, or by "bootstrapping" with successively better optimally designed filters. Edge-weighted ideals were created from the binary ideals with a subroutine that set a 2-pixel wide border to intensity 255 and the interior to intensity 128. The pixels at intensity 128 were ignored in the subsequent error minimization.

For the computer-generated Gaussian random noise images, the objects of interest were round with a known radius. The exact border was known by design and the ideal images were created to exactly match the synthetic objects.

LEAST SQUARES FILTER DESIGN

A. First Order (Linear) Filter Design

The steps in the image segmentation model can be defined as $$H = K*G + D \tag{1a}$$

$$S_{i,j} = B; H_{i,j} \leq T \tag{1b}$$

$$S_{i,j} = C; H_{i,j} > T \tag{1c}$$

where G is the original image, K is the discrete convolution kernel, H is the filtered image with indices i and j defining the two dimensional array of pixels, T is the threshold, S is the resulting segmented binary image, B and C are the two values of the binary image, D is a constant, and * is the discrete, 2D convolution operator. The zero order constant D was added to account for image offset.

The kernel can be designed to achieve exact binary values, or the threshold concept can be incorporated into the design algorithm. For the former case, the merit function is defined as $$E = \sum_j \sum_i (H_{i,j} - U_{i,j})^2 \tag{2}$$

where E is the error, H is the filtered image as above, and U is the user-defined ideal image. The indices i and j indicate summation over all interior image pixels where the convolution is explicitly defined. Wrap-around at the image borders was avoided by defining the filtered image to be smaller by an amount dependent on the kernel size. At any defined filtered image point, the convolution (with the additive constant removed) in (1) is explicitly written as $$H_{i,j} = \sum_{n=-p}^{p} \sum_{m=-p}^{p} K_{m,n} G_{i+m, j+n} \tag{3}$$

where K is the convolution kernel and m and n are the kernel indices spanning the neighborhood of the kernel. In a square, odd dimensioned kernel, the definition p=(dimension−1)/2 clarifies the summation index limits (e.g., p=1 in a 3×3 kernel, p=2 in a 5×5, etc.). The method of least squares error minimization is then applied to the merit function, equation (2), and the resulting set of linear equations are solved to obtain K, the linear, constant coefficient finite impulse response (FIR) filter that best maps G to U. The additive constant was included in all computations, but was removed from the derivations for simplicity.

Incorporation of the threshold into the design algorithm is achieved by defining the merit function as $$E=0; U_{i,j}=B, H_{i,j} \leq R \tag{4a}$$

$$E=0; U_{i,j}=C, H_{i,j} \geq Q \tag{4b}$$

$$E = \sum_j \sum_i (H_{i,j} - U_{i,j})^2; \text{otherwise} \tag{4c}$$

where U is a binary ideal image. The conditions in (4) make it piecewise differentiable. Although piecewise differentiability introduces the requirement for nonlinear, iterative minimization, these conditions allow results outside the minimum contrast range without penalty. The intensities defined by (R, Q) constitute the minimum contrast range. For 8-bit images, it is convenient to define R=0, Q=255. With no error, the filtered result contains object pixels ≥255 and background pixels ≤0, and segmentation is threshold independent in the 8-bit range. This range is arbitrary and may be changed for other grayscale resolutions.

With substitution of (3) into (4) and differentiation, the first derivative is $$\frac{\partial E}{\partial K_{q,r}} = 0 \; U_{i,j} = B, H_{i,j} \leq R \text{ or } U_{i,j} = C, H_{i,j} \geq Q \tag{5a}$$

$$\frac{\partial E}{\partial K_{q,r}} = \tag{5b}$$

$$2 \sum_j \sum_i \left( \left( \sum_{n=-p}^{p} \sum_{m=-p}^{p} K_{m,n} G_{i+m,j+n} \right) - U_{i,j} \right) G_{i+q,j+r}; \text{otherwise}$$

and the second derivative is $$\frac{\partial^2 E}{\partial K_{q,r} \partial K_{s,t}} = 2 \sum_j \sum_i A_{i,j} \tag{6a}$$

$$A_{i,j}=0; U_{i,j}=B, H_{i,j} \leq R \text{ or } U_{i,j}=C, H_{i,j} \geq Q \tag{6b}$$

$$A_{i,j}=(G_{i+q,j+r} G_{i+s,j+t}); \text{otherwise} \tag{6c}$$

The Levenberg-Marquardt method (W. H. Press, S. A. Teukolsky, W. T. Vetterling, and B. P. Flannery, *Numerical*

*Recipes in C*, 2nd ed., New York: Cambridge, 1992) can be used to efficiently find the minimum because of its ability to shift between methods of steepest gradient descent and quadratic approximation when appropriate. Making the following conventional definitions $$\vec{\beta} \equiv \frac{1}{2} \frac{\partial E}{\partial K_{q,r}} \tag{7a}$$

$$[\alpha] \equiv \frac{1}{2} \frac{\partial^2 E}{\partial K_{q,r} \partial K_{s,t}} \tag{7b}$$

$$\alpha'_{j,j} \equiv \alpha_{j,j}(1 + \lambda) \tag{7c}$$

$$\alpha'_{j,k} \equiv \alpha_{j,k}; (j \neq k) \tag{7d}$$

where $\lambda$ is a constant proportional to the iteration step size, an equation of the form $$[\alpha'] \vec{\delta k} = \vec{\beta} \tag{8}$$

may be solved repeatedly for additive kernel adjustments $\vec{\delta k}$ until a solution kernel $K = \Sigma \vec{\delta k}$ is reached.

The final generalization of the filter design procedure that was used to improve classification rate was the inclusion of a least squares weighting scheme. This weighting scheme is based on the principle that the border map completely defines the extent of a filled object. Such weighting is also justified by digital FIR filter theory. By neglecting the object interiors from the filter design stage, the filter can concentrate on the specific set of Fourier components representing the object boundaries, giving more accurate segmentation of the object borders for a given kernel size. If object borders are segmented to form a closed contour, any errors in the classification of object interior pixels can subsequently be corrected with the previously described fill routine, regardless of the severity of error. Thus, accurate boundary segmentation is sufficient for accurate object segmentation, and improvement in boundary segmentation should increase overall segmentation accuracy. To this end, the error function of (4) is redefined as $$E=0; U_{i,j}=B, H_{i,j} \leq R \tag{9a}$$

$$E=0; U_{i,j}=C, H_{i,j} \geq Q \tag{9b}$$

$$E = \sum_j \sum_i \Phi_{i,j}(H_{i,j} - U_{i,j})^2; \text{otherwise} \tag{9c}$$

where $\Phi$ is the user-defined weighting image. Equations (5), (6), (7), (8) and use of the Levenberg-Marquardt method follow in the same manner as before. Ill conditioning in the matrix equation (8) and the equivalent equation for the linear case (not shown) was avoided by use of a singular value decomposition of those equations. (W. H. Press et al., op cit.).

B. Second Order (Nonlinear) Filter Design

The methods for second order filter design are analogous to those for first order filter design. The difference is that K in equations 1a–c becomes a second order filter. There is no reason to assume that first order filters, or transforms (e.g., convolution, Fourier transform, sine transform, cosine transform) would be capable of creating thresholdable intensity contrast for all patterns. It is known, for example, that first order filters cannot separate differences in image variance or standard deviation (John C. Russ, *The Image Processing Handbook*, CRC Press: Boca Raton, pp. 238–243, 1992). The Fourier spectrum of random noise also looks like random noise, therefore first order filters cannot separate regions differing only by the standard deviation of the noise. Variance, however, is a second order characteristic that can be distinguished by a second order neighborhood operator. Analogous to the first order convolution filter, a second order neighborhood operator can be defined as $$H_{i,j} = K * G_{i,j} + (N * G_{i,j})^2 + P * G_{i,j}^2 \tag{10}$$

where N and P are new kernels and * is the standard convolution operator. This is a generalization of the variance operator since it can be shown that a particular set of values of K, N and P result in the variance. On the other hand, it is a special case of the most general second order operator, which contains parameters (kernel elements) for all the squares of the pixels in the neighborhood and parameters for all cross terms in the square of the neighborhood. For a 3×3 neighborhood the general second order operator, with the second order terms written out, is $$H_{i,j} = K * G_{i,j} + P_0 G_{i-1,j-1}^2 + P_1 G_{i-1,j}^2 + P_2 G_{i-1,j+1}^2 + P_3 G_{i,j-1}^2 + \tag{11}$$

$$P_4 G_{i,j}^2 + P_5 G_{i,j+1}^2 + P_6 G_{i+1,j-1}^2 + P_7 G_{i+1,j}^2 + P_8 G_{i+1,j+1}^2 +$$

$$A_{01} G_{i-1,j-1} G_{i-1,j} + A_{02} G_{i-1,j-1} G_{i-1,j+1} + A_{03} G_{i-1,j} G_{i,j-1} +$$

$$A_{04} G_{i-1,j-1} G_{i,j} + A_{05} G_{i-1,j-1} G_{i,j+1} + A_{06} G_{i-1,j-1} G_{i+1,j-1} +$$

$$A_{07} G_{i-1,j-1} G_{i+1,j} + A_{08} G_{i-1,j-1} G_{i+1,j+1} + A_{12} G_{i-1,j} G_{i-1,j+1} +$$

$$A_{13} G_{i-1,j} G_{i,j-1} + A_{14} G_{i-1,j} G_{i,j} + A_{15} G_{i-1,j} G_{i,j+1} + A_{16} G_{i-1,j} G_{i+1,j-1} +$$

$$A_{17} G_{i-1,j} G_{i+1,j} + A_{18} G_{i-1,j} G_{i+1,j+1} + A_{23} G_{i-1,j+1} G_{i,j-1} +$$

$$A_{24} G_{i-1,j+1} G_{i,j} + A_{25} G_{i-1,j+1} G_{i,j+1} + A_{26} G_{i-1,j+1} G_{i+1,j-1} +$$

$$A_{27} G_{i-1,j+1} G_{i+1,j} + A_{28} G_{i-1,j+1} G_{i+1,j+1} + A_{34} G_{i,j-1} G_{i,j} +$$

$$A_{35} G_{i,j-1} G_{i,j+1} + A_{36} G_{i,j-1} G_{i+1,j-1} + A_{37} G_{i,j-1} G_{i+1,j} +$$

$$A_{38} G_{i,j-1} G_{i+1,j+1} + A_{45} G_{i,j} G_{i,j+1} + A_{46} G_{i,j} G_{i+1,j-1} + A_{47} G_{i,j} G_{i+1,j} +$$

$$A_{48} G_{i,j} G_{i+1,j+1} + A_{56} G_{i,j+1} G_{i+1,j-1} + A_{57} G_{i,j+1} G_{i+1,j} +$$

$$A_{58} G_{i,j+1} G_{i+1,j+1} + A_{67} G_{i+1,j-1} G_{i+1,j} + A_{68} G_{i+1,j-1} G_{i+1,j+1} +$$

$$A_{78} G_{i+1,j} G_{i+1,j+1}$$

where A is the full set of cross terms only partially represented by N in equation 10. The simpler version contains 18 second order elements and the general version contains 45 second order terms. For an n×n filter, there are $2n^2$ second order terms for the simpler version and $n^2(n^2+1)/2$ second order terms for the general version.

The complete second order filter can be condensed into the following generating function $$H_{i,j} = C + \sum_{n=-p}^{p} \sum_{m=-p}^{p} K_{m,n} G_{i+m,j+n} + \tag{12}$$

$$\sum_{l=-p}^{p} \sum_{k=-p}^{p} \sum_{n=-p}^{p} \sum_{m=-p}^{p} \xi_{k,l,m,n} G_{i+m,j+n} G_{i+k,j+l}$$

where C is the zero-order (dc) term, $K_{m,n}$ is the first order (convolution) kernel, $\xi_{k,l,m,n}$ is the second order kernel (combining A and P in equation 11), and p, H, and G are defined as before. The general second order filter was used for the examples shown in the figures and discussed below.

Figure 6A:
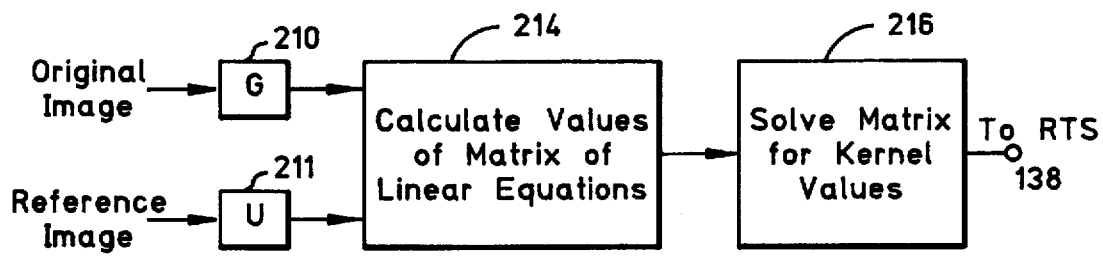
FIG. 6(a) and FIG. 6(b) are block diagrams illustrating two preferred embodiments of a process that implements the invention.
Figure 6B:
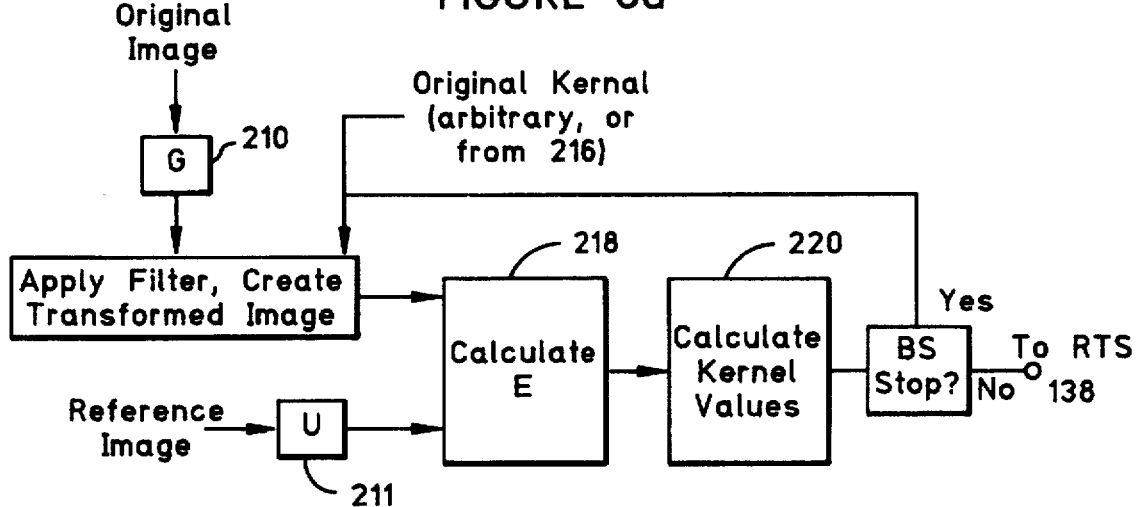

The process flow in the host computer 112 for the invention is illustrated in FIG. 6a (for the linear filter case) and FIG. 6b (for the non-linear filter case). The result in each case is an array of values corresponding to a neighborhood operator in the form of a filter kernel. In FIG. 6a, the array of pixels corresponding to the original image G is acquired by the host computer 112 and placed in a buffer 210, while the array of pixels corresponding to the reference image is acquired and placed in the buffer 211. Using the intensity values of the pixels stored in the two buffers 210 and 211, the values of a matrix of linear equations are calculated by the host computer 112 in step 214 according to equations (2)–(8), and equations (9a)–(9c) are obtained and solved at 216 according to the Levenberg-Marquardt method discussed above.

For the non-linear case, the pixel arrays corresponding to the original and reference images are obtained and stored in host computer buffers 210 and 211. Then the merit values are calculated by process 218 in host computer 112 and used in equation (12) to generate the kernel values for a second-order filter. These kernel values are entered into the RTS 138 of the image processor.

Figure 7:
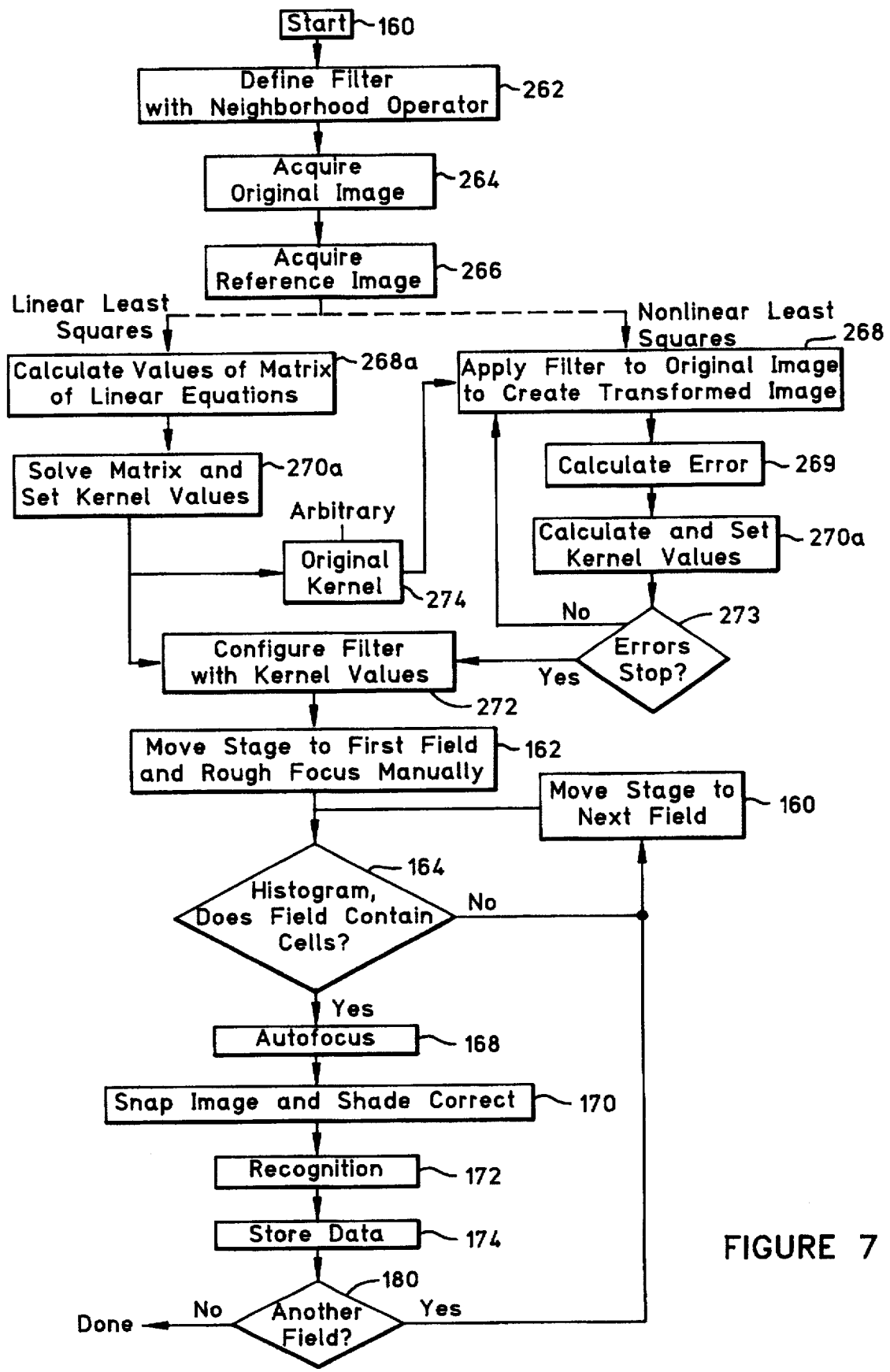
FIG. 7 is a flow diagram of a computer program that embodies the invention and controls the image cytometer of FIG. 2.

FIG. 7 illustrates the incorporation of the invention into a process for controlling the cytometer 100 (FIG. 2), beginning at a start state 160. Prior to starting the cytometry process, a scanning area is defined, a shade correction image is calculated, and gain and offset on the image processor in camera are set. Gain and offset are adjusted with the aid of a histogram overlay to view the range of image intensities. The histogram overlay is a graphical plot of pixel numbers versus intensity, created from the histogram array provided by the image processor 110. This plot is overlaid on the image displayed on monitor 139 driven by the image processor 110. These adjustments are made to set the background to zero intensity and ensure that the intensities fall as much as possible within the measurement range of the system (for example, an 8-bit range of 0 to 255).

FIG. 7 represents the software 113 (FIG. 2) installed and executed in the host computer 112 (FIG. 2). Although the software was written in C, those skilled in the art will recognize the steps in the flow diagram of FIG. 7 can be implemented by using a number of different compilers and/or programming languages.

From start state 160, the cytometer 100 moves to a state 262 where a digital filter is defined. The digital filter may, for example, be a convolution filter defined by a neighborhood operator in the form of a kernel. The definition in this case includes specifying the shape and size of the kernel. Those skilled in the art will realize that other digital filter implementations, each with a particular kind of neighborhood operator, can be defined in this step. For example, the digital filter can comprise a Volterra filter, whose neighborhood operator is a Volterra series.

Next, the first array of pixels corresponding to the original image is acquired at step 264, while the second array of pixels corresponding to the reference image is acquired at step 266. In this regard, the reference image may be acquired as described in connection with FIG. 5 by drawing a perimeter around an object in an image or image portion displayed on the monitor 139. According to the invention, all pixels outside the perimeter are treated as background pixels, while all pixels inside are treated as object pixels. If weighting is used, as laid out in equations (9a)–(9c), pixel weights may be assigned in step 266. According to the invention, pixels are assigned weights according to whether they are in the background, adjacent or on the perimeter, or in the object. Preferably, the weights are binary, with a "1" being assigned to pixels on or adjacent the perimeter. Background and object pixels may be both weighted by "0"; or, either may be weighted by "0" according to the desired objective. The pixel weights are stored in the host processor 112.

Next, according to whether a linear or non-linear least filter design process has been chosen, the processing of the host computer 112, using pixel values of the reference image, calculates values of the matrix of linear equations in step 268a and solves the matrix for kernel parameter values in step 270a using linear least squares or calculates merit function values in step 268b and calculates, and sets kernel parameter values in step 270b for nonlinear least squares. The kernel values are used to configure the kernel of the RTS 138.

Next, assuming that a convolution filter has been defined in step 262, an original kernel is used by the host computer 110 to create a transformed image in step 268b. Then, in step 269, the error is calculated according to equations (4a)–(4b), if weighting is not used, and according to equations (9a)–(9c), if weighting is used. In step 270a, the kernel values for the filter are calculated according to equations (7a)–(7d) and (8). In step 273, successive error values calculated in step 269 are compared against an error change value. If the difference between the merit values for two successive sets of kernel values is greater than the error change value, the positive exit is taken from step 273 and the kernel and error values are adjusted and recalculated; otherwise, the process exits to step 272.

It is pointed out that the calculation of filter values using nonlinear least squares can use preset kernel values. These values, set in step 274, may be obtained from a linear filter matrix (step 270a) or set arbitrarily when the filter is defined.

In step 272 the host computer 112 enters the kernel values into the RTS 138, if a linear convolution filter was defined in step 262, or the kernel values are retained in the host computer if another neighborhood operator such as the second order filter or Volterra series was chosen in step 262. This kernel is used in the recognition step 172. If the kernel is part of a convolution filter, the recognition step 172 is carried out in real time with the help of the RTS 138 and if the kernel is part of a second order filter, Volterra series, or another neighborhood operator the recognition step is carried out by the host computer 112. Next, in state 162, the cytometer 100 sets up a first field. For example, the scanning area for a 20×objective may comprise 8,000 fields, or images embodied in 512×480 pixel arrays, that are each approximately 250×330 microns. The motorized stage 103 (FIG. 2) is moved to a first field and microscope 102 has been focused manually for an initial, rough focus.

In state 164, the cytometer 100 tests whether the field under consideration contains any cells. Movement to a new field occurs at state 166 if image intensity is too low to contain a nucleus (or when analysis of one field is complete). For example, if there are less than 810 pixels of intensity greater than 35, autofocus is not performed. This number of pixels is calculated from the image histogram. By definition, adjacent fields do not overlap and nuclei touching the image border are ignored. If an image is bright enough to contain a nucleus, then the cytometer 100 proceeds from the decision state 164 to an autofocus state 168.

Autofocus is the requirement for any fully automated microscope-based image processing system. Autofocus is necessary because of the small depth of the field in the microscope 102 (FIG. 2), typically on the order of a micron. Autofocus is controlled from the host computer 112 (FIG. 2). The host computer 112 can perform a transformation on the image to obtain a value which represents a degree of focus. This value can then be compared with another value obtained from another image after the stage 103 has moved up or down via the XYZ stage controller 106.

After autofocus, the image cytometer 100 proceeds to a state 170 to "snap", or acquire, a new image from the CCD camera 108 through the ADI 130, and shade corrects the image. Each time an image is acquired for analysis, it must be shade corrected to compensate for uneven illumination. Shade correction is performed by multiplying the new image with the correction image which is prestored in the host processor 112. The shade correction image is calculated from a flat-field image.

After shade correction of the digital image, the image cytometer 100 moves to recognition, or image separation, function 172. Recognition is the conversion of the array of pixels making up a digital image into an accurate, easily-accessible representation of the image objects in the memory of the host computer 112.

The simplest way for a computer to identify pixels is by differences in intensity, that is, in a continuous tone or grayscale image. DAPI stained cells create images of high contrast, facilitating recognition. Even with this high contrast, however, it is not possible to accurately recognize all nuclei by a single intensity range. This is due to the fact that the edges in images often exhibit a gradual, rather than an abrupt change in intensity from object background. The immediate background of brighter nuclei is often equal to or greater than the intensity of dimmer nuclei. If the threshold is low enough to include the dimmest nuclei, the selection of the brightest ones contains a significant number of background pixels, or image points.

This problem is overcome by application of digital filtering and object intensity dependent thresholding in the recognition function of 172. The digital filter applied is the one defined and configured in steps 262-272 according to the invention and then determines a threshold value to select nuclei in the image.

After the recognition, where image segmentation of a field, the image cytometer 100 continues to a state 174 to store the object data on a hard disk (not shown) of the host computer 112. If, at the subsequent decision state 180, it is determined that more fields of the specimen 114 (FIG. 2) need to be processed, then the image cytometer program proceeds to state 160 to begin another cycle with a new field. Otherwise, if all fields have been processed, the program terminates at an ended state DONE.

VALIDATION BY DESIGN OF KNOWN FILTERS

Synthetic examples are presented first to validate the model and least squares solution methods. Validation was performed by derivation of filters from synthetic image pairs related by known filters. Refer now to FIGS. 8 and 9, in which FIG. 8 shows (a) a complicated scene with an object intensity of 30, (b) a Laplacian filtered version of 'a', and (c) a version of 'b' thresholded at an intensity of 1. The arrows are oriented in the direction of the mapping and the convolution kernels between mappings were derived by least squares. All filter results were clipped to (0, 255). FIG. 9 shows (a) an original image of character 'E' at an intensity of 100, (b) the vertical edge of the filtered 'E', (c) the blurred image of the 'E' and (d) the result of attempting to find the inverse filter for the blur. Although an exact inverse filter could not be found (broken line), the exact segmentation filter for the thresholded ideal 'E' in (e) is shown. The arrows are oriented in the direction of the mapping. The convolution kernels between forward mappings were derived by nonlinear least squares, and the inverse mapping by linear least squares. All filter results were clipped to (0, 255). Vertical edge detection, Laplacian and lowpass filters were applied to synthetic input images with straight and circular edges in FIG. 8 and straight edges in FIG. 9. The lowpass filter in FIG. 9 was also used to demonstrate solving for the inverse transfer function. Linear least squares minimization was used for the inverse in FIG. 9 and nonlinear, unweighted methods ($\Phi=1$ for all i, j) were used in the filter designs with R=0 and Q=255 in equations (4), to show the effect of familiar kernels that produce values outside the grayscale range. In the experiments where the intensities were between 0 and 255, the minimum contrast requirement did not apply and there was an exact mapping. In these cases, the nonlinear model converged to the same result as the linear one.

Figure 8A:
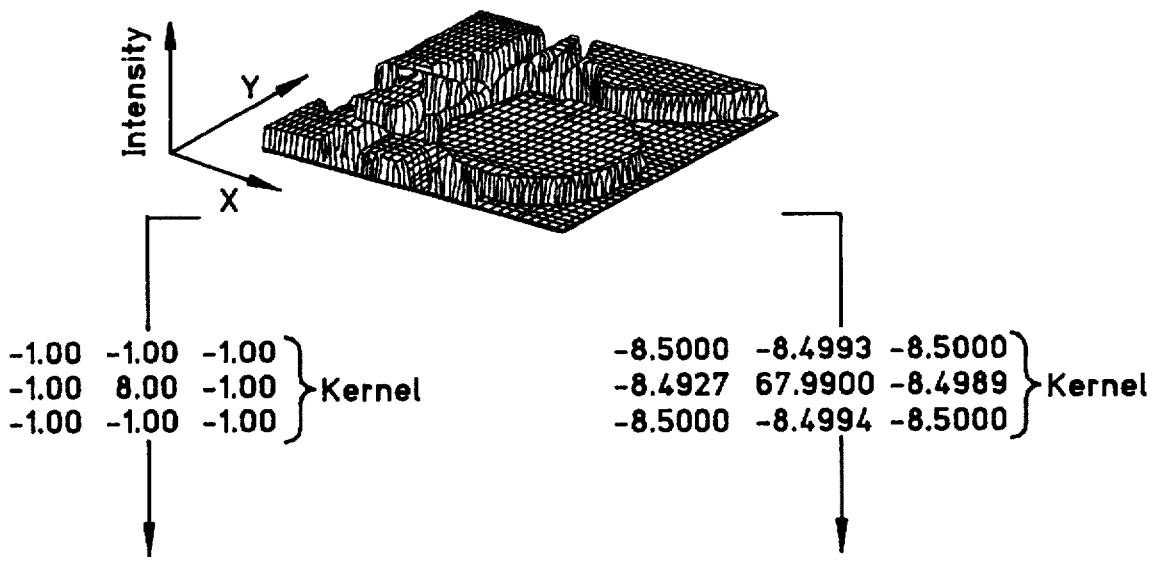
FIG. 8 illustrates two mappings between synthetic images for validation on complicated edge shapes with curves.
Figure 8B:
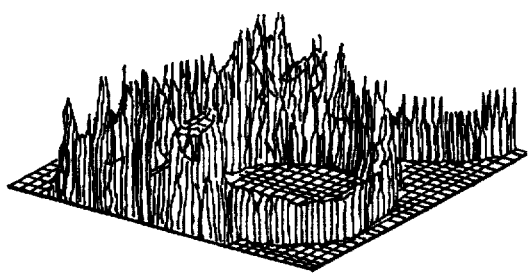
Figure 8C:
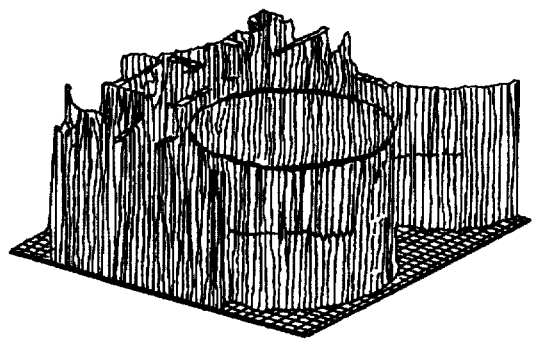

FIG. 8 demonstrates the first set of synthetic image experiments. FIG. 8(a) represents a complex scene on the scale of a 3×3 neighborhood, with objects (at intensity=30) that exhibit a mixture of all possible edge orientations. FIG. 8(b) is the Laplacian of FIG. 8(a) and FIG. 8(c) is a threshold of 8(b) at intensity 1. The experiment of defining the filter mapping FIGS. 8(a→b) resulted in the same Laplacian kernel used to create FIG. 8(b). The fact that the scene of FIG. 8(a) has approximately equal amounts of all possible edge orientations in a 3×3 neighborhood means no orientations are preferred and the symmetry of the kernel is preserved. This is not true when all edge orientations are not present in the image (data not shown). If, for example, the image pair to which a Laplacian is applied has only vertical edge elements, the derived corner kernel elements are less in magnitude than the east/west elements and the north/south elements remain 0. If only horizontal and vertical edges are present, the derived corner elements still remain less in magnitude than the compass point kernel elements.

The experiment defining the mapping FIGS. 8(b→c) resulted in a kernel that has symmetry similar to the traditional Laplacian kernel. Since FIG. 8(c) is a binary version of the Laplacian of the input (i.e. edges=255, all else=0), knowledge of the truncating character of the system was exploited to derive a kernel that mapped the input image into the intensities beyond the minimum background intensity of 0 and the maximum object intensity of 255. Note that excepting the 8-bit digitization error, this kernel is the filter of FIGS. 8(a→b) scaled by a factor of 8.5. This scale was exactly the factor necessary to increase the lowest edge intensities of FIG. 8(b) to 255. This is not the only kernel that will correctly perform the FIG. 8(a→c) mapping. Any multiple of the FIGS. 8(a→b) Laplacian greater than 8.5 will generate FIG. 8(c) after truncation to (0, 255). This demonstrates that a zero-error multidimensional plane can occur in the parameter space of the merit function. When this occurs, iteration will cease when the first zero-error parameter set is found and the result may depend on the initial seed values. Minimum magnitude parameters may have been found for this example with all seed values at 0.

FIG. 9 shows a series of results from input and output images based on an image of the letter 'E' with an input intensity of 100. The image of FIG. 9(b) was created from the image of FIG. 9(a) with a 3×3 vertical edge enhancing kernel. An experiment was performed to determine the optimal kernel mapping FIG. 9(a) into FIG. 9(b). The result, shown on the figure, is exactly that used in creation of FIG. 9(b). As in the FIGS. 8(a→b) mapping, a many of the intensities were between 0 and 255 and a single exact fit was found.

Figure 9E:
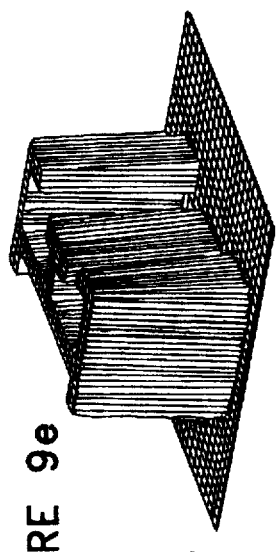
FIG. 9 illustrates two mappings, a vertical edge detector and a blur, with an attempt to carry out the inverse of the blur.
Figure 9D:
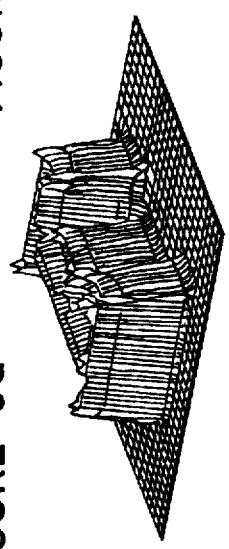
Figure 9A:
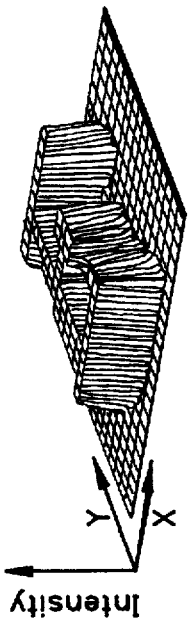
Figure 9C:
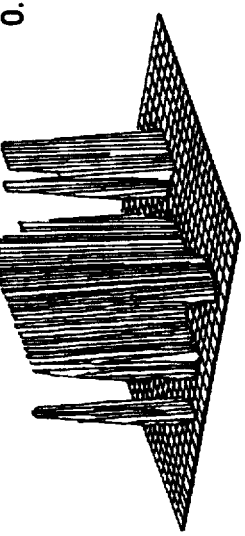
Figure 9B:
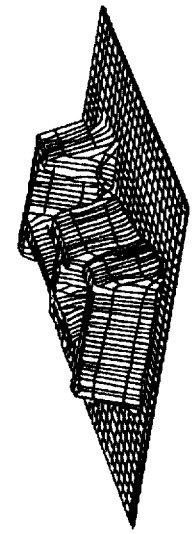

The second mapping in FIG. 9 was used to demonstrate the advantages of the image segmentation model in cases where there is no inverse transfer function. FIG. 9(c) is the result of a 3×3 Gaussian lowpass filter with a target value of ¼, compass point values of ⅛ and corner values of ⅟₁₆. The kernel derived from the FIGS. 9(a→c) mapping is identical to the filter used in creating FIG. 9(c), within the 8-bit digitization error of the images. Next, derivation of the inverse mapping of FIGS. 9(c→a) was performed using linear least squares. In this case an exact mapping was not achieved. This derivation resulted in the image of FIG. 9(d)

rather than FIG. 9(a). The problem is that an exact inverse filter does not exist. This was verified by examining the Fourier spectrum of the blur filter padded with zeroes to 512×512 (data not shown). About 25% of the Fourier coefficients have a magnitude at or near zero and, therefore, cannot be inverted. FIG. 9(d) shows the problem of reconstructing edges after a lowpass filter that, for a linear system, irretrievably attenuates some of the high frequencies. The analogous segmentation mapping from the blurred image is shown by the ideal in FIG. 9(e), a binary version of FIG. 9(a) thresholded at an intensity of 1. An exact solution for the mapping of FIGS. 9(c→e) was found using the nonlinear model.

The optical transfer function (OTF) of the microscope is more complicated than the blur filter in FIG. 9, but it is basically a lowpass filter. Problems inverting the microscope OTF because of its lowpass characteristics have motivated nonlinear deconvolution techniques for deblurring fluorescence microscope images. (D. A. Agard, Y. Hiraoka, P. Shaw and J. W. Sedat, "Fluorescence Microscopy in Three Dimensions," in *Fluorescence Microscopy of Living Cells in Culture*, Part B, D. L. Taylor and Y.-L. Wang, eds., Academic: San Diego, 1989) and (W. A. Carrington, K. E. Fogarty, L. Lifschitz and F. S. Fay, "Three-dimensional Imaging on Confocal and Wide-Field Microscopes," in *Handbook of Biological Confocal Microscopy*, J. Pawley ed., Plenum: New York, 1990). Thus, the problems of using linear deconvolution to reconstruct blurred images are well known. Requiring minimum contrast for accurate image segmentation is less demanding for the linear convolution operator than attempting complete image restoration. FIG. 9 demonstrates that an exact image segmentation mapping may exist even when the inverse transfer function does not.

These experiments indicate that the least squares methods and image segmentation model give expected results on synthetic images with known transfer functions. Therefore, they should produce optimal filters for segmentation of cell nuclei, where the transfer function is unknown.

SEGMENTATION OF IMAGES OF CELL NUCLEI

Figure 1:
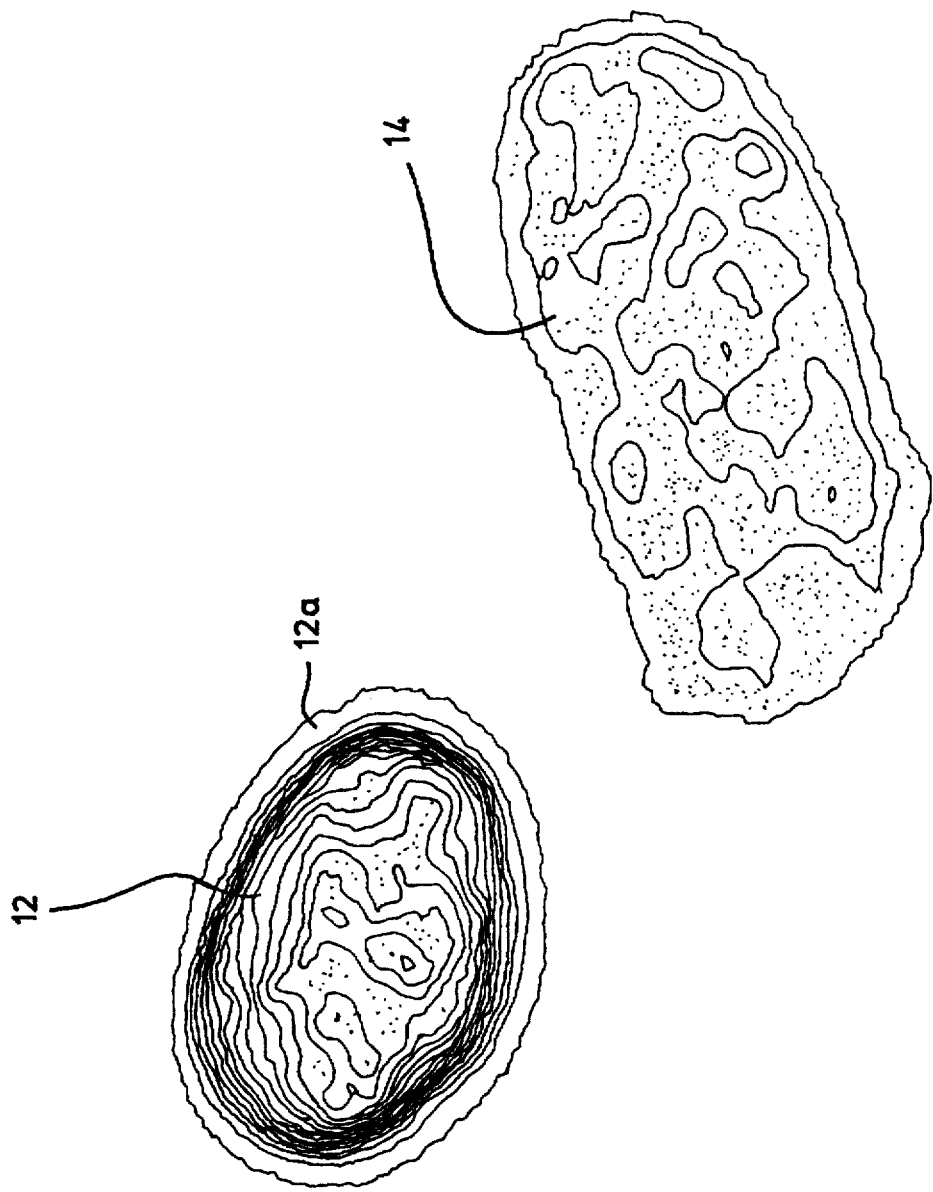
FIG. 1. represents an intensity contour plot of a photomicrograph of a problematic scenario in images of fluorescent stained cells. The object 12 in the upper-left is a mitotic figure containing a much higher density of cellular DNA than the dimmer resting cell 14 in the lower right. The bright halo 12a in the vicinity of the mitotic figure is not part of the cell nucleus, and makes accurate segmentation of the objects impossible with a single, global intensity threshold. Lower intensities are enhanced. Field is 60 μm horizontally.

Refer now to FIG. 10, in which (a) is a 3D plot of a microscopically-acquired, raw input image of FIG. 1, (b) represents an optimally-thresholded raw input showing over selection of pixels in the bright nucleus and underselection of in the dim nucleus resulting in indentations (arrow), (c) shows a user-defined unweighted binary ideal image, and (d) illustrates a weighted binary ideal image with object interior pixels at an intensity of 128 to indicate least squares weighting coefficient Φ=0 for this region. In FIG. 10 the valid object perimeter, at an intensity of 255, is 2 pixels wide. Plots are shown at a zoom of 0.5 for clarity, making the perimeter appear 1 pixel wide.

Figure 10A:
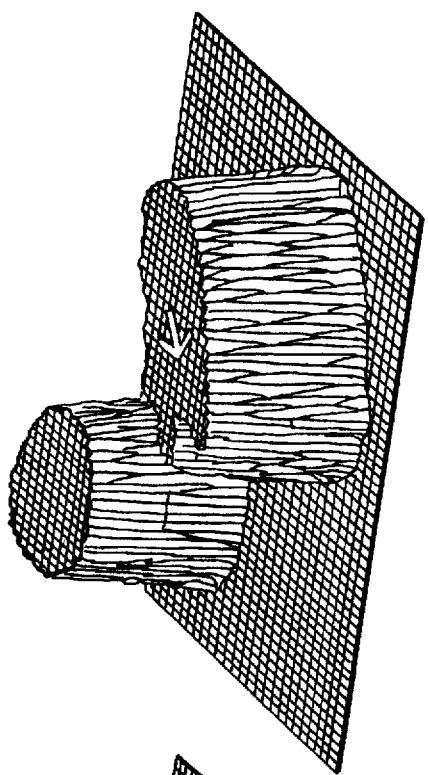
FIG. 10 illustrates raw and ideal images of fluorescent stained cell nuclei.

The image segmentation problems caused by the marked contrast between different fluorescent stained cell nuclei can be examined more closely in the 3D plot of FIG. 10(a), representing the image in FIG. 1. The inflection points at the edge of the bright nucleus are considerably higher in intensity than any portion of dim nucleus. It is also easy to see that both edges exhibit gradually increasing intensity toward the inflection points. This makes it impossible to choose a threshold that works well for both nuclei. With the variations in intensity at the edge of the dim nucleus, it is unlikely that a single threshold would work well even for the same portions of this single object.

Figure 10B:
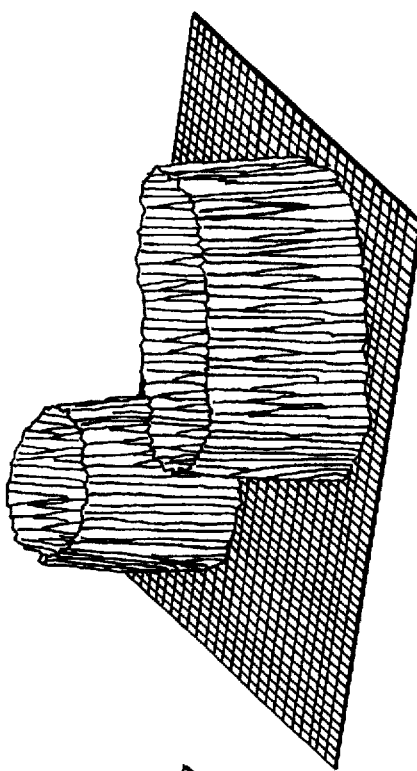
Figure 10C:
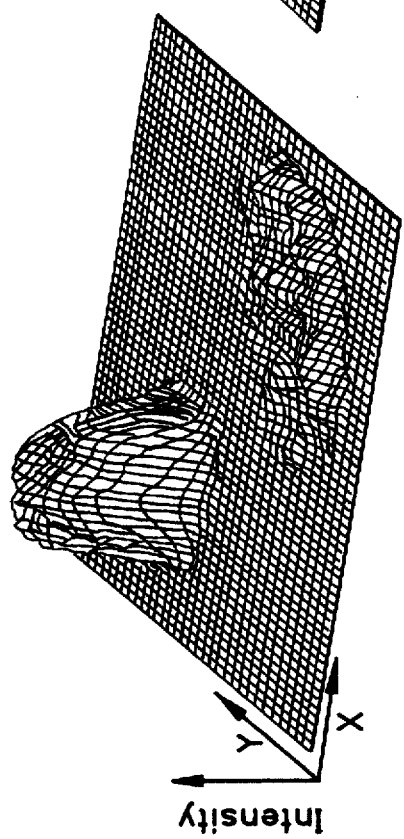
Figure 10D:
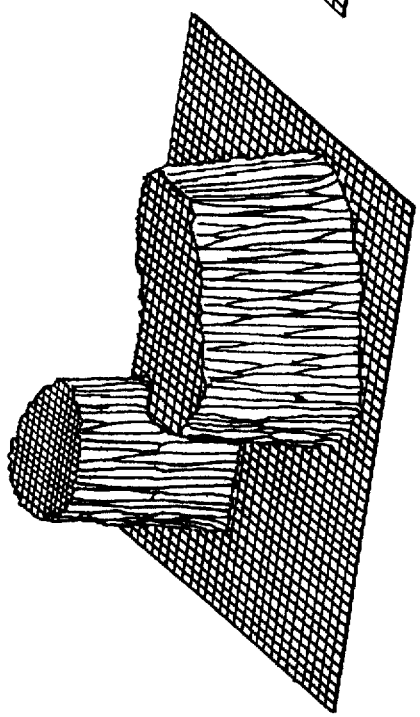

These problems are further illustrated by the optimally thresholded binary image (threshold=10) plotted in FIG. 10(b). The optimal threshold was determined by comparing the results of all possible thresholds (0–255) with the predefined ideal binary image of FIG. 10(c). Further comparisons can be made using the edge only version of the ideal binary image, shown in FIG. 10(d). The visible errors include the indentations at locations (see arrow) where the edge of the resting nucleus was particularly dim and the over selection of pixels in the brighter nucleus. The compromise forced between erroneous inclusion of background pixels adjacent to the mitotic nucleus and exclusion of dim pixels from the resting nucleus contributed to misclassification of 17% of the pixels at the optimal threshold.

Figure 11:
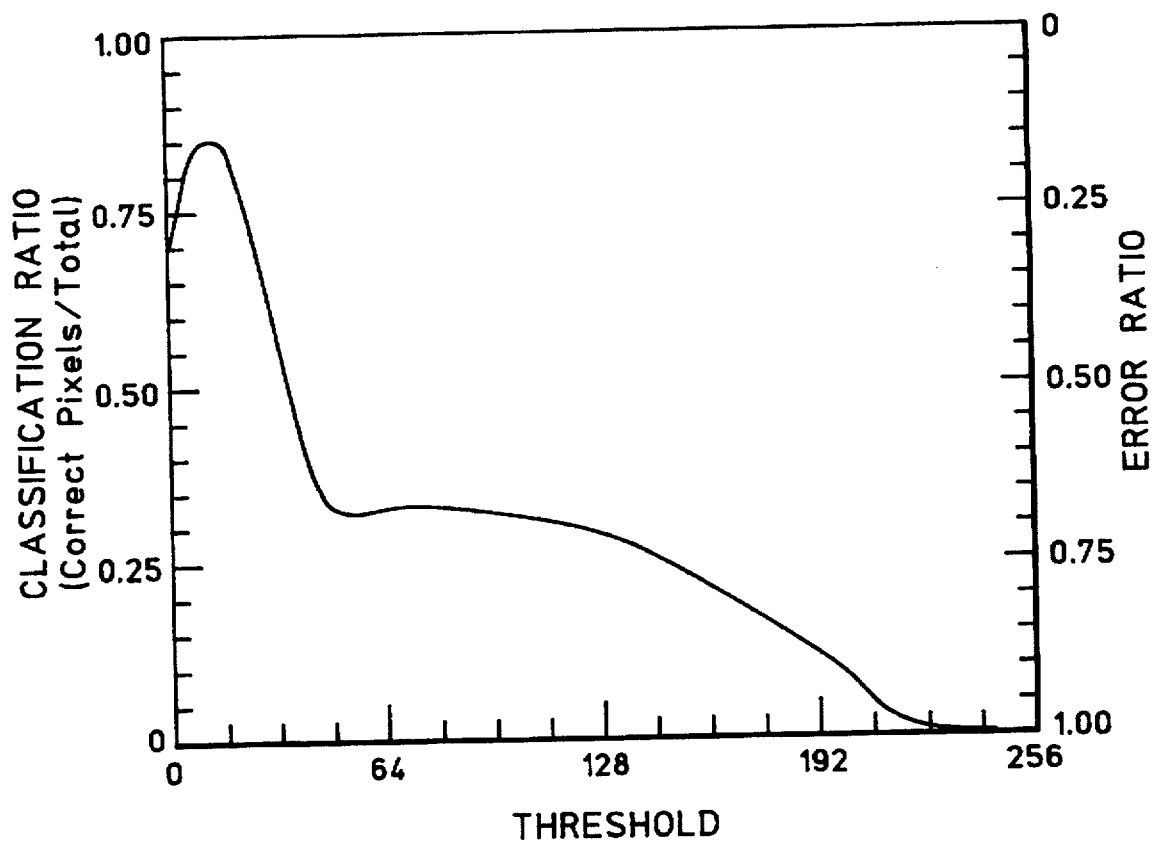
FIG. 11 is a graph showing threshold sensitivity to pixel intensity in a raw input image.

Unfortunately, it is not possible to segment large numbers of images at optimal threshold levels, as these values would be a function of the random distribution of objects of varying intensity throughout the specimen and could not be predicted in advance. Slight deviations from the optimal thresholds could have a catastrophic impact on segmentation. For example, if upon segmentation of FIG. 10(a), the actual threshold value were chosen lower than the optimal value, non-object pixels located beneath the intensity-inflection object boundary would be included, drastically reducing the classification rate. Alternatively, if the threshold value were chosen somewhat higher than the optimal value, the segment of the mitotic nucleus might not be too severely distorted, but that of the dimmer, resting nucleus would become very severely attenuated, with large portions of pixels misclassified as background. The combined effects of this threshold sensitivity are illustrated by the plot of the classification ratio as a function of threshold in FIG. 11 in which the classification (error) ratio of FIG. 10(a) is shown as a function of threshold. The bimodal shape is due to the fact that the large dim nucleus has a low optimal threshold and the small bright one a relatively high optimal threshold. The combined optimal threshold is at an intensity of 10 with 17% pixel classification error and the average error is 72% over (0, 255). On either side of the peak in correct classification, the above effects caused increased error. The average error, or inverse of the classification ratio, over all thresholds was 72%. The average error is a better description because prediction of the optimal threshold is impossible or impractical. If the average error were zero, segmentation accuracy would be threshold independent. Practically, low error in a predictable, but smaller range would be acceptable.

A. Conventional Sharpen and Linearly Designed Filters

Refer now to FIG. 12, which shows the first set of experiments directed at decreasing threshold sensitivity involving the use of generic and linearly designed filters. In FIG. 12 conventional sharpen and linearly designed filter results from application to the image of FIG. 10(a) are shown. In this figure, (a) shows a 3×3 sharpen with a target of 9 and −1 elsewhere, (b) shows a linearly designed 3×3 filter result, (c) shows a linearly designed 9×9 filter result, and (d) shows a linearly designed 13×13 filter result. There is contrast improvement in both objects in (b), (c), and (d) over (a), but the differences between the different kernel sizes are more difficult to discern. The results of these filters are presented together in FIG. 12 because the appearance of the filtered images and the segmentation improvements were similar. FIG. 12(a) shows the result of the a 3×3 sharpen filter (center of kernel 9, all others −1). This filter made the edges sharper, reducing the probability of incorrectly segmenting the brighter mitotic nucleus. The problem was that the conventional sharpen did not isolate the intensity inflections at the border, but also enhanced interior gradients. Intensities at the bottom of an interior valley were sometimes pushed transformed to 0 or below. A hole filling routine could correct this indiscriminate sharpening if the valleys did not extend to the edge. Unfortunately, as is seen in the example, such gradients can lie near the edge in resting nuclei.

Figure 12A:
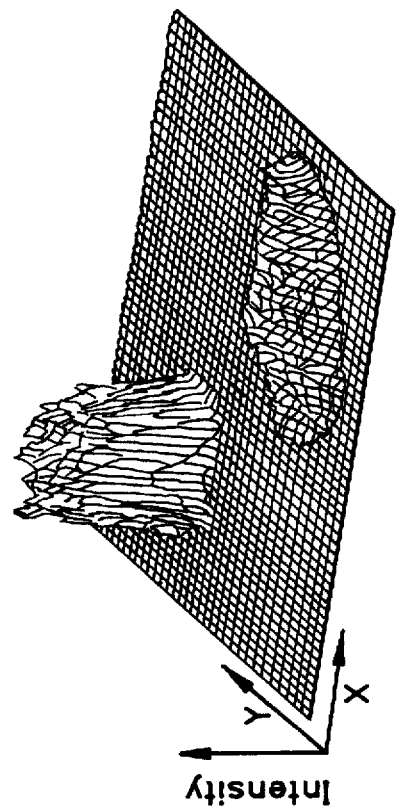
FIG. 12 illustrates segmentation results obtained through the use of generic and linear filters.
Figure 12B:
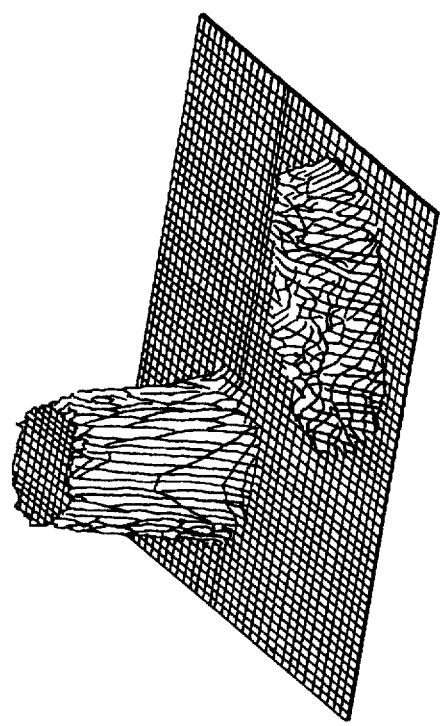
Figure 12C:
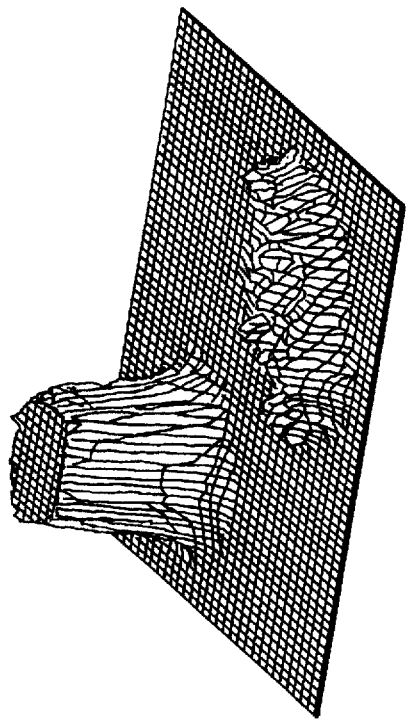
Figure 12D:
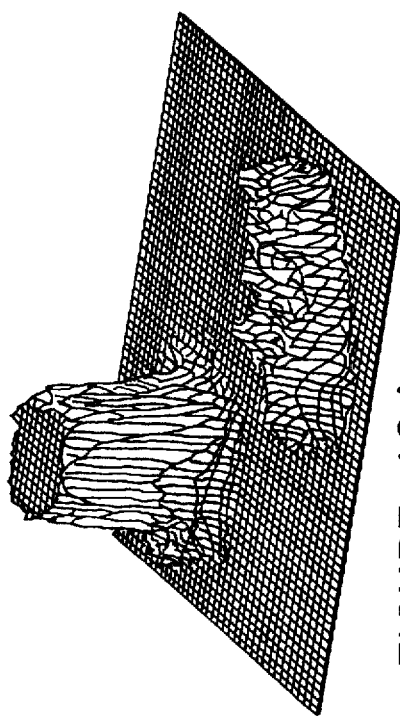

The 3×3, 9×9 and 13×13 linearly derived filter results are shown in FIGS. 12(b), 12(c) and 12(d), respectively. The appearance of the resting nucleus in all three of these figures is remarkably similar to that of the same segment in FIG. 12(a). The linearly designed filters successively increase the brightness of the resting nucleus, but the tradeoff between improving the highpass characteristics necessary for sharpening the mitotic nucleus and retaining some of the lowpass characteristics needed to overcome the problem of the internal gradients was not eliminated by this technique. With the two larger convolution filters, the ringing also become visible, first with the mitotic nucleus and then the resting nucleus. This ringing is the same well known pattern that arises when using a finite number of frequencies to represent a square wave in 1D data. Ringing in the image arose from the attempt to map the input image to the nearly square edge of the ideal image.

Figure 13:
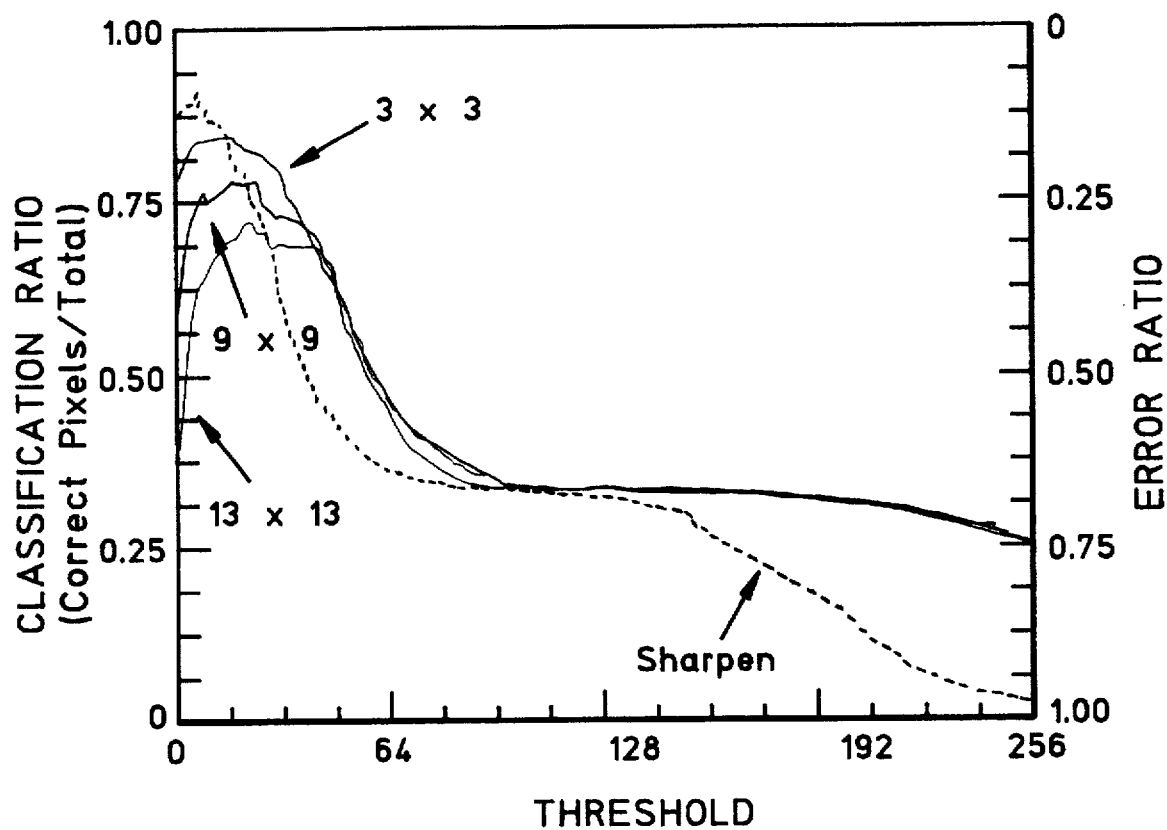
FIG. 13 is a graph showing classification ratio in a cytometer as a function of threshold for the filters represented in FIG. 12.
Figure 14A:
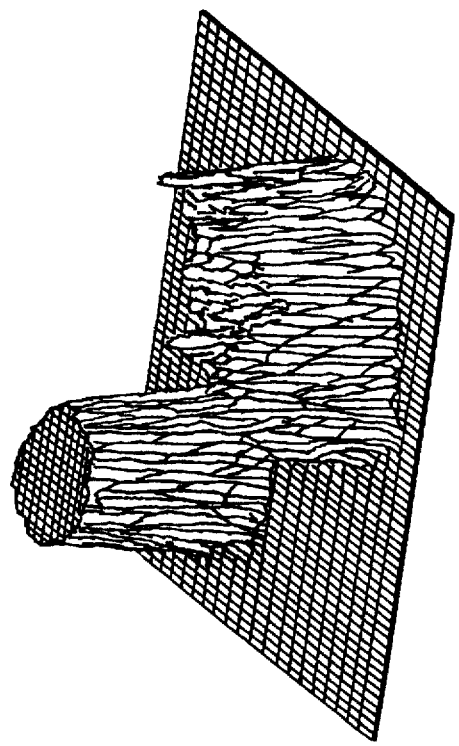
FIG. 14 illustrates results obtained by filters designed by non-linear minimization of error.
Figure 14B:
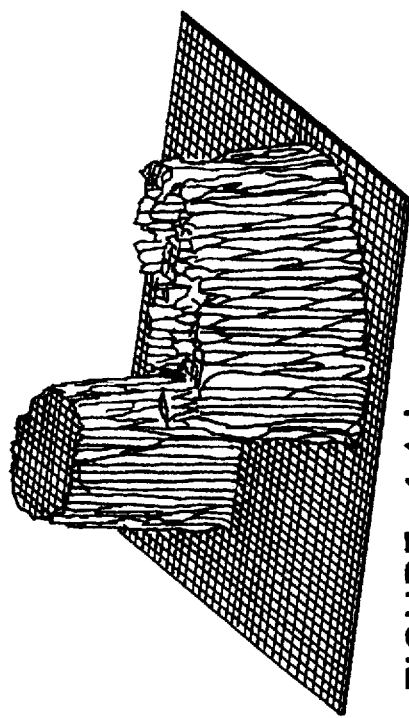
Figure 14C:
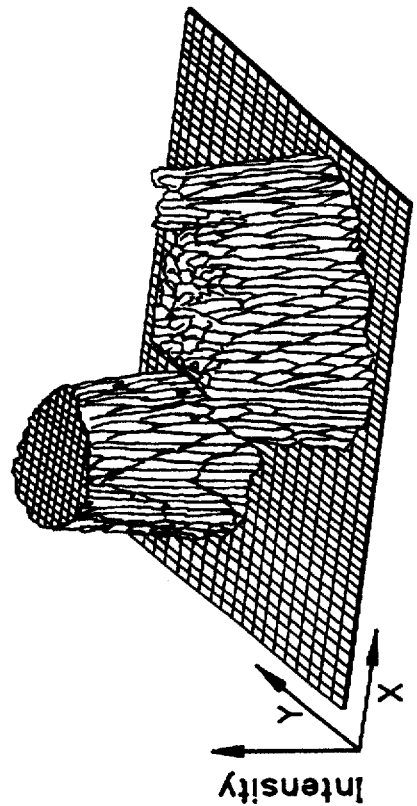
Figure 14D:
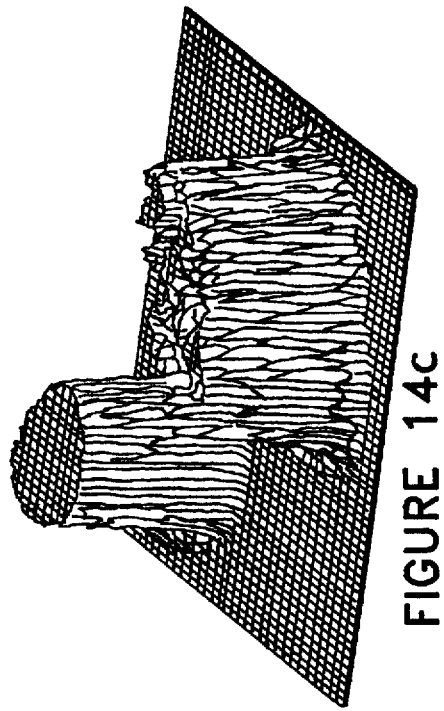

The classification ratio as a function of threshold for these four filters is shown in FIG. 13, in which the peak error ratio worsened and the average error ratio improved with increasing kernel size. The shape of the curves is similar to the classification ratio of the raw input image given in FIG. 11, but the widths of the curves increase with the size of the filter. It is interesting that the error ratio, or inverse of the classification ratio, at optimal threshold actually increases from the sharpen filter to the largest linearly designed filter (10%, 16%, 22% and 28%, respectively). This is because the merit function (equation (2)) is the sum of the squares of the differences between the input and ideal pixels, not the classification error ratio. The average error ratio over the threshold range is a more direct measure of the effects of this merit function. The average error ratios with the filters used in FIG. 13 were 68%, 42%, 41% and 40%, respectively. Thus, error minimization with an exact mapping decreased the sensitivity of segmentation to the threshold value, but left important errors. Furthermore, the relatively small improvement from a 3×3 to a 13×13 convolution suggested that derivation of larger filters would not be useful.

B. Nonlinearly Designed Filters

The experiments with linearly designed filters indicate that requiring an exact mapping between input and ideal images unnecessarily constrains the design. The exact mapping is unnecessary because correct segmentation requires only that the object pixels be above, and background pixels below, the threshold. This leads to the merit function in equations (4) for designing filters yielding minimum object-background contrast. FIGS. 14(a–d) illustrate the application of four filters designed by nonlinear minimization of error, in which 14(a) shows an unweighted 3×3 filter result, 14(b) shows a weighted 3×3 filter result, 14(c) shows an unweighted 13×13 filter result, and 14(d) shows a weighted 13×13 filter result. The shape of the edges and the object-background contrast of both nuclei improved dramatically over FIG. 12. These figures exhibit a substantially different appearance than the sharpen and linearly designed filter results shown previously. The object-background contrast is much greater, especially with the resting nucleus. In both nuclei, there were dramatic improvements in object boundary slope and inflection coincidence. The indentations on the right side of the mitotic nucleus and the left side of the resting nucleus in FIG. 12 were essentially eliminated. In spite of the small size of the 3×3 filters used for FIGS. 14(a) and 14(b), the results appear much better than the 13×13 linearly designed filter. Even further improvement is observed with the nonlinearly designed 13×13 filter results shown in FIGS. 14(c) and 14(d). The differences between the unweighted and weighted designs in FIGS. 14(a,c) and FIGS. 14(b,d), respectively, are less obvious. Some of the edge regions of FIG. 14(b) appear to have higher contrast and others appear lower. The weighted 13×13 result in FIG. 14(d), however, appears to have consistently greater edge slope than the unweighted result in FIG. 14(c).

Figure 15:
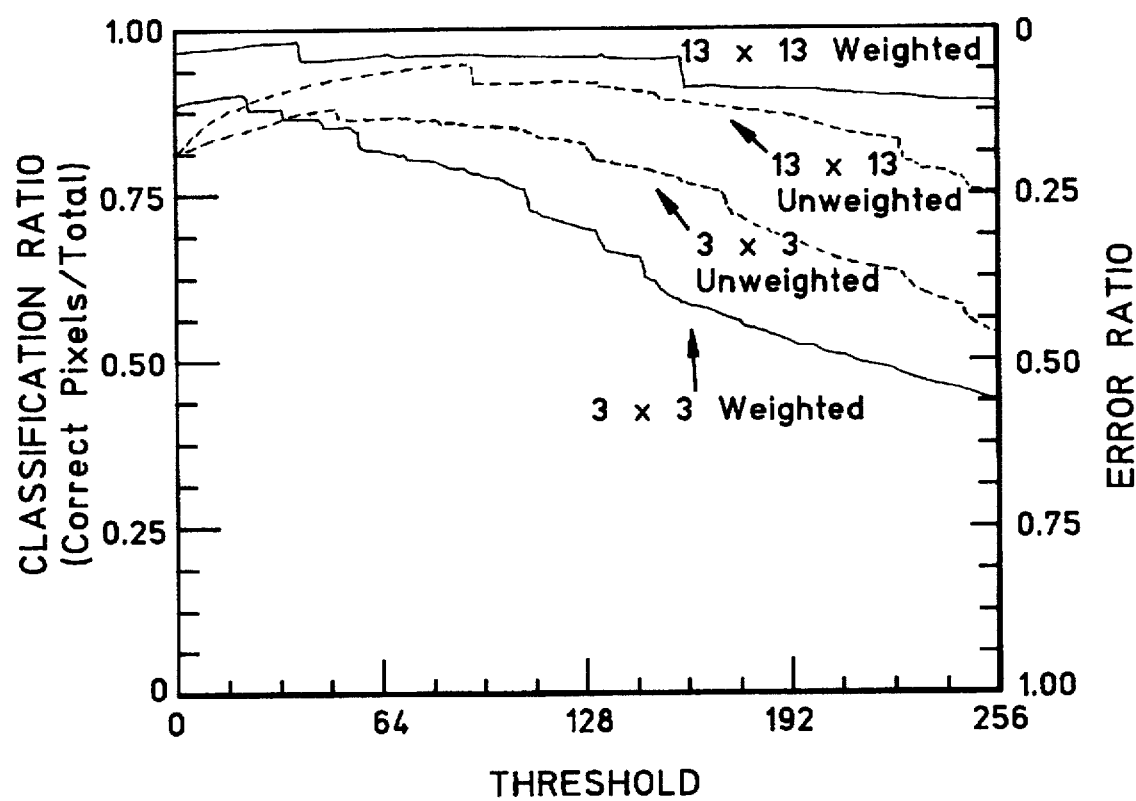
FIG. 15 is a plot illustrating classification ratios achieved for the non-linearly designed filters whose results are shown in FIG. 14.

The classification ratios for the nonlinearly designed filters are shown in FIG. 15. In FIG. 15 the plots for the 3×3 unweighted and weighted filters cross due to a progressively more broken edge in the weighted version. For the 13×13 weighted filter results, the error ratio at the optimal threshold is 2% and the average error ratio over (0, 255) is 8%. These results are much different in shape from all previous classification ratio results, indicating substantially greater threshold insensitivity. The optimally thresholded and average error ratios for the 3×3 unweighted results are 12% and 23%, respectively, whereas the 3×3 weighted error ratios are 10% and 32%, respectively. Thus the optimally thresholded error ratio decreased and the average error ratio increased with addition of the edge weighting. This discrepancy is probably due to the more incomplete formation of the edge with the smaller filter. The weighting forced the merit function to operate only for a 2-pixel wide edge mask of the object. The resulting decreased interior object intensities can be observed by comparing FIG. 14(b) to FIG. 14(a).

The effects of breaking the edge with increasing threshold intensity can also be seen in FIG. 15. The plot of the 3×3 weighted filter shows many more downward jump discontinuities than visible in the 3×3 unweighted curve. These discontinuities arise from the hole filling step. Holes are filled only when the boundary is completely closed. As the threshold increases, breaks in the boundary are accompanied by loss of the correction applied to interior pixels below the threshold. Since interior pixel enhancement is sacrificed to improve edge enhancement, the interior errors are greater with the weighted than unweighted design. The use of a 2-pixel wide, rather than a 1-pixel wide edge weighting decreases this problem somewhat. Other edge weighting schemes, such as radially dependent weights may further improve the small kernel results. The same shape differences between the 13×13 weighted and unweighted results are visible with the plots of the classification ratios, but the curves do not cross and the weighted classification rate was found to be consistently better. The optimally thresholded and average error ratios for the 13×13 unweighted designs are 5.4% and 12%, respectively, and for the 13×13 weighted designs are 2% and 8%, respectively. Thus, the larger kernel is better able to produce unbroken edges and simultaneously maintain interior enhancement.

C. Spectral Analysis

Figure 16A:
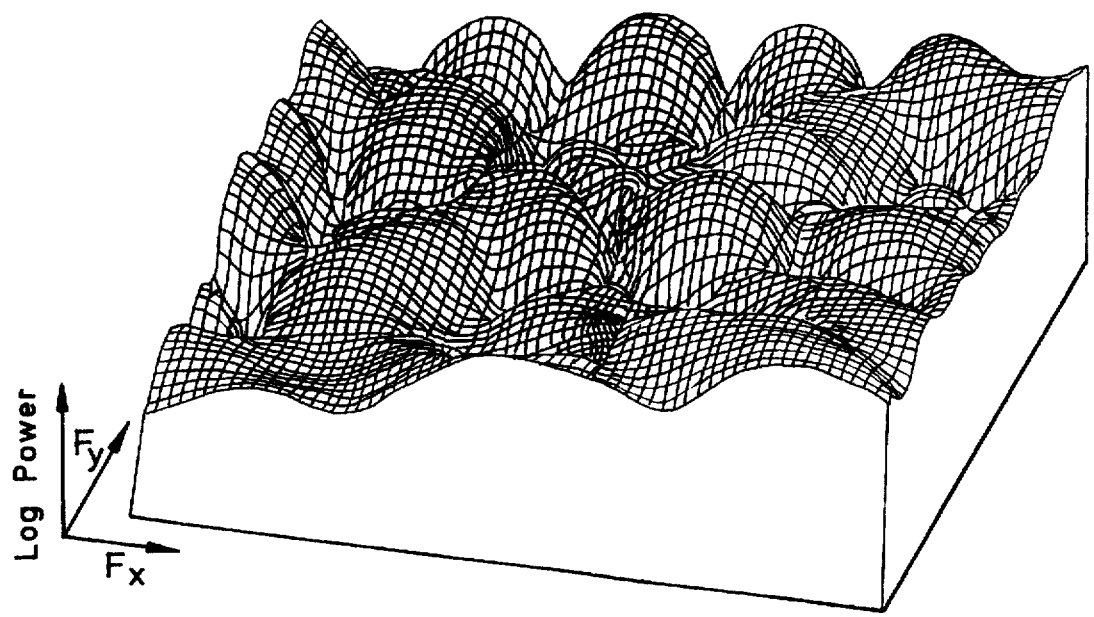
FIG. 16 is a plot illustrating the log power spectrum and phase response for a digital filter including a 13×13 kernel.
Figure 16B:
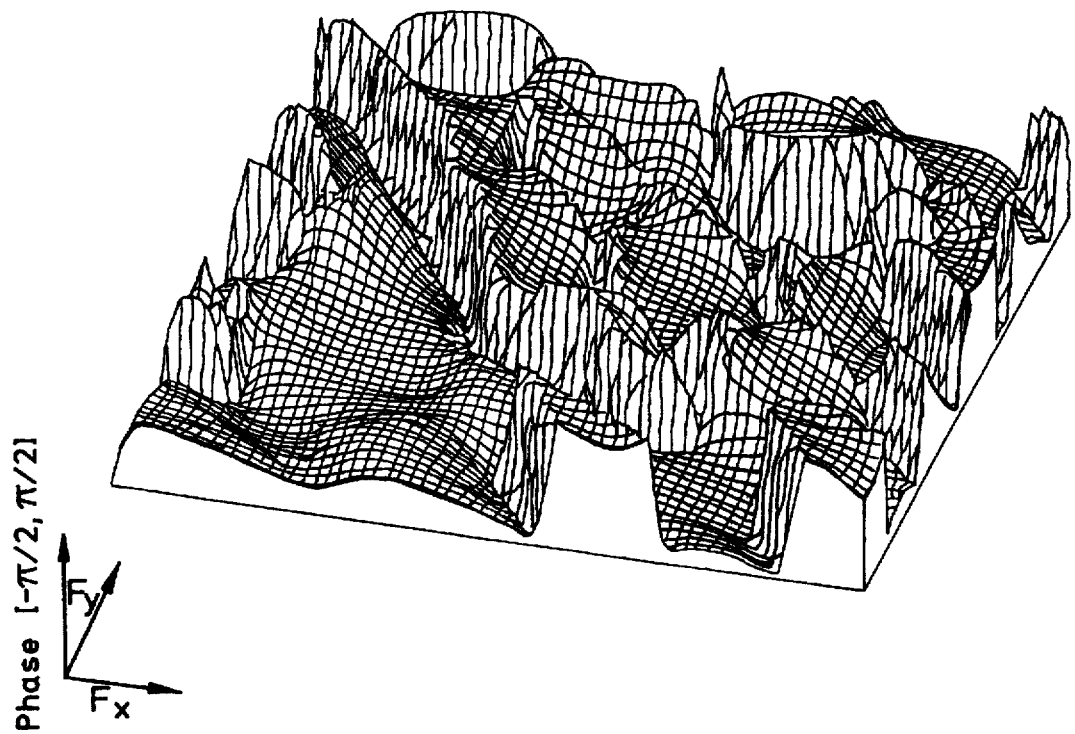

The assumption that bandpass filter design techniques would be inappropriate for this image segmentation problem was made based on the appearances of the nuclei and supported by the failure of the sharpen filter. The derived filters should also provide an indication of the degree of spectral complexity of the segmentation transfer function. FIG. 16 illustrates (a) the log power spectrum and (b) phase response for the best filter, the 13×13 kernel designed with the nonlinear, weighted least squares method and padded to 512×512. Only the positive quadrant is shown. These are complicated spectra considering the size of the kernel. The power spectrum clearly does not represent any kind of simplified bandpass filter and the phase response is not linear or zero. The complexity of these plots supports the conclusion that frequency domain specification of optimal filters for segmentation may be impractical or even impossible. The spectra support the original hypothesis that conventional bandpass design techniques were unlikely to achieve accurate image segmentation filters, given the complexity of the images. Since this is an optimal filter, the spectral and phase complexity may be important in image segmentation filters for this application. Although some of this complexity may be due to forcing the task of optimally filtering on a relatively small filter, it is also plausible that it is necessary for accurate segmentation.

SEGMENTATION OF SYNTHETIC SECOND ORDER IMAGE PATTERNS

FIG. 17 shows an example of second order image properties in objects that were segmented by a second order Volterra filter. FIG. 17(a) shows the original pattern created from a commercially available random noise generating subroutine (William H. Press, Saul A. Teukolsky, William T. Vetterling, and Brian P. Flannery, *Numerical Recipes in C*, 2nd ed., Cambridge U. Press:Cambridge, pp. 274–328, 1992). Both the inner circular area and the background intensity means are 128. The standard deviation of the inner circular area is 10, and the standard deviation of the background is 34. FIG. 17(b) shows the essentially useless application of a first order sharpening convolution filter, from Nickolls et al. (P. Nickolls, J. Piper, D. Rutovitz, A. Chisholm, I. Johnstone, and M. Robertson, "Pre-processing of images in an automated chromosome analysis system," *Pattern Recognition*, Vol. 14, pp. 219–229, 1981) on FIG. 17(a). Note that no noticeable enhancement toward image segmentation has taken place. Rather, the standard deviation of both regions has been increased by the sharpening, or high pass filter affect of the 7×7 Laplacian. FIG. 17(c) shows the result of filtering FIG. 17(a) with the best 7×7 general second order Volterra filter. The advantage of this filter is obvious. High contrast with very good edge enhancement occurred using the second order filter. This edge enhancement does not occur when a simple neighborhood variance (or standard deviation) neighborhood operator is applied to these images. FIG. 17(d) shows the completion of the image segmentation step with an intensity threshold at 128. Image segmentation has been carried out with a high degree of accuracy (error on the order of one pixel width around the border of the object) Thus, application of the perceptron criterion to design of second order Volterra filters can segment image patterns that cannot be segmented by first order filters. Successful image segmentation on the model image in FIG. 17 indicates that microscope images with cellular and tissue components differing by higher order image properties will segment accurately with choice and design of the proper Volterra filter.

DISCUSSION AND CONCLUSIONS

Incorporation of the threshold into filter design using the perceptron criterion has resulted in a high degree of accuracy for real time segmentation of the test image. The minimum error was 2% for the best filter. The sensitivity of this error to the choice of threshold was also very low, nominally <5% error over a threshold range of (0, 150). This compares favorably with 17% error at the best threshold and 72% average error over the entire threshold range for the raw image. It is likely that 2% error is the minimum achievable given the probability of an imperfect ideal image. A test image with high internuclear contrast and internal structure was specifically chosen to challenge the filter design methods. The large, obscure resting cell nucleus was represented by intensities very near 0 in some regions, whereas the smaller, bright mitotic nucleus had intensities near 255. Images with greater internuclear contrast would have been outside the digital intrascene dynamic range and would have changed the problem to one of a loss of information. The success of the filter design method on this difficult image suggests that it may be generally applicable to real time segmentation of images of fluorescent stained cell nuclei that fall within the intrascene dynamic range.

The limited intrascene dynamic range contributes to the difficulty in segmenting these images. If the dynamic range and sensitivity were greater, the edges of the dim nuclei would contain greater intensity gradients and higher frequency components. The frequency characteristics of the edges of the dim nuclei would be closer to the characteristics of the bright nuclei and segmentation might be achieved with a highpass, or bandpass filter. It is unlikely, however, that improvements in camera sensitivity and dynamic range alone will make the methods developed here obsolete. This is because DAPI-stained cell nuclei are among the brightest fluorescent biological specimens available, due to the unusually high concentration of a single substance (DNA) in the nucleus, and a particularly bright, specific fluorochrome (DAPI). Even if camera dynamic range and sensitivity increase enough to make a simple bandpass filter on DAPI-stained specimens acceptable, there are still be many other fluorescent specimens at lower intensity limits. As video cameras continue to improve, it will simply become possible to apply real time analysis to a wider variety of more obscure specimens.

The frequency and intensity characteristics of this image segmentation problem were appropriate for the proposed model. With a fluorescent dye like DAPI that is specific for the major component of the object of interest, segmentation problem could have relied on thresholding if the optics were perfect. With less than perfect optics, the resulting blur makes simple thresholding inaccurate. If the blur is due to linear aberrations, then correction might be possible with a linear filter. The image segmentation model incorporated the ability to correct for linear sources of blur that can also be corrected by linear deconvolution. The advantage of the present approach over deconvolution is that it may also yield the best linear correction of nonlinear sources of degradation, a claim that cannot be made of linear deconvolution implemented with the inverse of the OTF. In addition, deconvolution requires estimates of singular components of the inverse OTF, whereas even in the presence of singularities in the inverse OTF, this least squares method will find an optimal solution.

It is interesting to note that with all the variations of filters applied, from 3×3 sharpen and linearly designed 3×3 through 13×13 filters to nonlinearly designed filters, the biggest improvement came from incorporating the threshold into the model. With both the linearly and nonlinearly designed filters, changing from a 3×3 filter with 9 parameters to a 13×13 filter with 169 parameters did not yield as much improvement as freeing the design constraints from an exact mapping to the ideal image. Incorporation of the threshold into filter design thus allows much more efficient use of a given convolution filter size. Since the cost of real time hardware grows essentially linearly with the number of parameters in the kernel, efficient use is particularly important in this application. Edge weighting improved the operation of a given size kernel even more, but not as much as the incorporation of the threshold through minimum contrast. In spite of the importance of Fourier theory and the wealth of digital signal processing techniques, segmentation accuracy here depended less on the size of the convolution kernel than on incorporation of minimum contrast.

It may be useful in othto applications as well, to utilize an image segmentation model to take advantage of the fact that each pixel is transformed into a segmented value corresponding to its object class. The work presented here on segmenting images of fluorescent stained nuclei is a specific implementation of such a model and imposes the constraint of real time operation. Other images, however, would not necessarily involve this particular set of characteristics, and different models that incorporate segmentation as a mapping, rather than a model of the source image, might be useful. The mapping may be generalized to more than one object class, for example, each with its own non-overlapping minimum contrast range, and the convolution or Fourier filter could be replaced by other linear or nonlinear neighborhood operators. An example of this was provided in the accurate segmentation of the Gaussian noise image using a second order Volterra filter. This indicates the broad usefulness of utilizing the perceptron criterion to design filters for image segmentation by application of the appropriate filter followed by thresholding. The results support the conclusion that with proper design techniques, filters are capable of accurate segmentation of spectrally complicated fluorescent labeled objects and more complicated segmentation/recognition tasks requiring higher order, nonlinear neighborhood operators.

We claim:

1. A computer-executed method of separating an object from a background in a pixelated image with a best-designed digital filter, the method comprising:

selecting a digital filter for creating contrast in an image, the digital filter including a neighboring operator of second or higher order for processing neighborhoods of pixels in pixel array;

setting a contrast range (R,Q) in which R<Q;

receiving a first pixel array defining a pixelated image including one or more objects and a background;

applying the digital filter to the first pixel array to create a filtered image;

receiving a second pixel array defining a reference image, the reference image including at least one object included in the pixelated image and a background, in which pixels included in the at least one object are distinguished from pixels included in the background by a predetermined amount of contrast;

determining a merit function value by:
setting the merit function value to a specified value if, either a pixel in the background of the pixelated image is less than or equal to R and a corresponding pixel in the reference image is in a background of the reference image, or a pixel in an object of the pixelated image is greater than or equal to Q and a corresponding pixel in the reference image is an object of the reference image; or,
calculating a minimum merit function value otherwise;

changing the neighborhood operator of the digital filter to a new neighborhood operator in response to a minimum merit function value; and creating a segmented image in which an object of the pixelated image is separated from the background in the pixelated image by applying the digital filter with a new neighborhood operator to the pixelated image.

2. The method of claim 1, wherein the neighborhood operator is a convolution kernel.

3. The method of claim 1, wherein the neighborhood operator is a second order filter.

4. The method of claim 1, wherein the neighborhood operator is a Volterra series.

5. The method of claim 1, wherein determining includes thresholding the merit function value by:

causing the merit function value to equal zero when:
the pixel in the background of the pixelated image is less than or equal to R and the corresponding pixel in the reference image has a magnitude equal to a predetermined background value, or the pixel in the object of the pixelated image is greater than or equal to Q and the corresponding pixel in the reference image has a magnitude equal to a predetermined object value; or calculating a positive, non-zero merit function value otherwise.

6. The method of claim 5 further including deriving a transformed image by filtering a third pixel array with the digital filter, using the new neighborhood operator.

7. The method of claim 1, wherein the one or more objects are cells, or portions of cells.

8. The method of claim 1, wherein receiving a second pixel array includes:

buffering the second pixel array;

and determining further includes:
defining an array of weights, each weight corresponding to a location of one of the pixels in the reference image; and
multiplying the merit function value by a weight at the corresponding reference image pixel location to create a weighted merit function value.

9. The method of claim 8, wherein the weights are 1 at or adjacent edges of the one or more objects and 0 elsewhere in the one or more objects.

10. The method of claim 8, wherein the weights are 1 at or adjacent edges of the one or more objects, 0 inside the one or more objects, and 0 in the background.

11. The method of claim 8, wherein determining further includes thresholding the merit function value by:

causing the merit function value to equal zero when:
the pixel in the background of the pixelated image is less than or equal to R and the corresponding pixel in the reference image has a magnitude equal to a predetermined background value, or the pixel in the object of the pixelated image is greater than or equal to Q and the corresponding pixel in the reference image has a magnitude equal to a predetermined object value; or calculating a positive, non-zero merit function value otherwise.

12. A method executable on a computer for separating an object from a background in a pixelated image with a best-designed digital filter, the method comprising:

defining a type of digital filter, the digital filter including a neighborhood operator of second or higher order for processing neighborhoods of pixels in a pixel array;

setting a contrast range (R,Q) in which R<Q;

receiving a first pixel array defining a pixelated image including one or more objects and a background;

applying the digital filter to the first pixel array to create a first filtered image;

receiving a second pixel array defining a reference image, the reference image including at least one object included in the pixelated image and a background, in which pixels included in the at least one object are distinguished from pixels included in the background by a predetermined amount of contrast;

determining a merit function value by:
setting the merit function value to a specified value if, either a pixel in the background of the pixelated image is less than or equal to R and a corresponding pixel in the reference image is in a background of the reference image, or a pixel in an object of the pixelated image is greater than or equal to Q and a corresponding pixel in the reference image is in an object of the reference image; or, calculating a minimum merit function value otherwise;

computing values of neighborhood operator elements in response to the merit function value;

receiving a third pixel array defining an image including one or more objects and a background;

applying the digital filter to the third pixel array to create a second filtered image; and creating a segmented image in which an object of the image is separated from the background in the image by thresholding the second filtered image.

13. The method of claim 12, wherein the neighborhood operator is a convolution kernel.

14. The method of claim 12, wherein the neighborhood operator is a second order filter.

15. The method of claim 12, wherein the neighborhood operator is a Volterra series.

16. The method of claim 12, wherein determining includes thresholding the merit function value by:

causing the merit function value to equal zero when:
the pixel in the background of the pixelated image is less than or equal to R and the corresponding pixel in the reference image has a magnitude equal to a predetermined background value, or the pixel in the object of the pixelated image is greater than or equal to Q and the corresponding pixel in the reference image has a magnitude equal to a predetermined object value; or calculating a positive, non-zero merit function value otherwise.

17. The method of claim 16, wherein the one or more objects are cells, or portions of cells.

18. The method of claim 12, wherein receiving a second pixel array includes:

buffering the second pixel array;

and determining further includes:
defining an array of weights, each weight corresponding to a location of one of the pixels in the reference image; and multiplying the merit function value by a weight at the corresponding reference image pixel location to create a weighted merit function value.

19. The method of claim 18, wherein the weights are 1 at or adjacent edges of the one or more objects and 0 elsewhere in the one or more objects.

20. The method of claim 18, wherein the weights are 1 at or adjacent edges of the one or more objects, 0 inside the one or more objects, and 0 elsewhere in the background.

21. The method of claim 18 wherein further includes:

causing the merit function value to equal zero when:
the pixel in the background of the pixelated image is less than or equal to R and the corresponding pixel in the reference image has a magnitude equal to a predetermined background value, or the pixel in the object of the pixelated image is greater than or equal to Q and the corresponding pixel in the reference image has a magnitude equal to a predetermined object value; or calculating a positive, non-zero merit function value otherwise.

22. The method of claim 12, wherein applying the digital filter to the third pixel array creates or enhances contrast between the one or more objects and the background.

23. An image segmentation system, comprising:

means for acquiring an array of pixels defining a pixelated image including one or more objects and a background;

a digital filter for producing a transformed array of pixels representing the transformation of a pixelated image, the digital filter including a neighborhood operator of second or higher order for processing intensities of pixels in a pixel array;

means coupled to the means for acquiring and to the digital filter for setting values of the neighborhood operator in response to a first pixel array defining a pixelated image including one or more objects and a background and a second pixel array defining a reference image, the reference image including at least one object included in the pixelated image and a background in which pixels included in the at least one object are distinguished from pixels included in the background by a predetermined amount of contrast;

means for determining a merit function value by:
the pixel in the background of the pixelated image is less than or equal to R and the corresponding pixel in the reference image has a magnitude equal to a predetermined background value, or the pixel in the object of the pixelated image is greater than or equal to Q and the corresponding pixel in the reference image has a magnitude equal to a predetermined object value; or calculating a positive, non-zero merit function value otherwise;

means for changing the neighborhood operator to a new neighborhood operator in response to a minimum merit function value; and means for applying the new neighborhood operator of the digital filter to a third array of pixels defining an image to be segmented, the image to be segmented including one or more objects and a background, such that the new neighborhood operator creates or enhances contrast between the one or more objects in the background.

* * * * *

UNITED STATES PATENT AND TRADEMARK OFFICE
CERTIFICATE OF CORRECTION

PATENT NO.   : 5,790,692
DATED        : August 4, 1998
INVENTOR(S)  : Price et al It is certified that error appears in the above-identified patent and that said Letters Patent is hereby corrected as shown below:

Column 27, line 55, insert --deter mining-- between "wherein" and "further";

Column 28, line 35, insert --causing the merit function to equal zero when-- before the first occurrence of "the".

Signed and Sealed this

Twenty-ninth Day of December, 1998

Attest:

BRUCE LEHMAN

*Attesting Officer*    *Commissioner of Patents and Trademarks*